United States Patent

Yamazaki et al.

[19]

[11] Patent Number: 5,816,703
[45] Date of Patent: Oct. 6, 1998

[54] METHOD OF DETECTING DEFECTS OF A STRUCTURE

[75] Inventors: Kenichiro Yamazaki, Tokyo; Kiyotaka Kawase, Niigata; Toshio Koike, Tokyo; Susumu Harashima, Tokyo, all of Japan

[73] Assignee: Nittco Chemical Industry Co., Ltd., Tokyo, Japan

[21] Appl. No.: 688,849

[22] Filed: Jul. 31, 1996

[30] Foreign Application Priority Data

Nov. 29, 1995 [JP] Japan .................................... 7-311143
Nov. 29, 1995 [JP] Japan .................................... 7-311144
Jan. 11, 1996 [JP] Japan .................................... 8-002954
Apr. 18, 1996 [JP] Japan .................................... 8-096782

[51] Int. Cl.⁶ .................................................. G01N 25/72
[52] U.S. Cl. ........................... 374/4; 374/121; 374/5
[58] Field of Search .................. 374/4, 5, 6, 7, 374/121

[56] References Cited

U.S. PATENT DOCUMENTS 3,504,524  4/1970  Maley .......................................... 374/5
4,872,762  10/1989  Koshihara et al. ....................... 374/5

FOREIGN PATENT DOCUMENTS 0304708  3/1989  European Pat. Off. ................ 374/4
0054242  3/1989  Japan ........................................ 374/4
0214749  8/1989  Japan ........................................ 374/4
0319708  11/1971  U.S.S.R. ................................... 374/4
2164147  3/1986  United Kingdom ..................... 374/4
2168494  6/1986  United Kingdom ..................... 374/5

Primary Examiner—Diego F.F. Gutierrez
Attorney, Agent, or Firm—Andrus, Sceales, Starke & Sawall

[57] ABSTRACT

A method of detecting a defect on the surface of a structure using an infrared radiometric thermometer. It is determined that there is a lifting defect at a region of the surface if the region has a temperature difference of 0.3° C. or more in comparison with a surrounding region and has an area of 200 cm² or more. The temperature of the surface of the structure is obtained using the infrared radiometric thermometer in a period of time from 19:00 p.m. on a day when it is clear at least in the daytime to 4:30 a.m. on the next day.

9 Claims, 27 Drawing Sheets

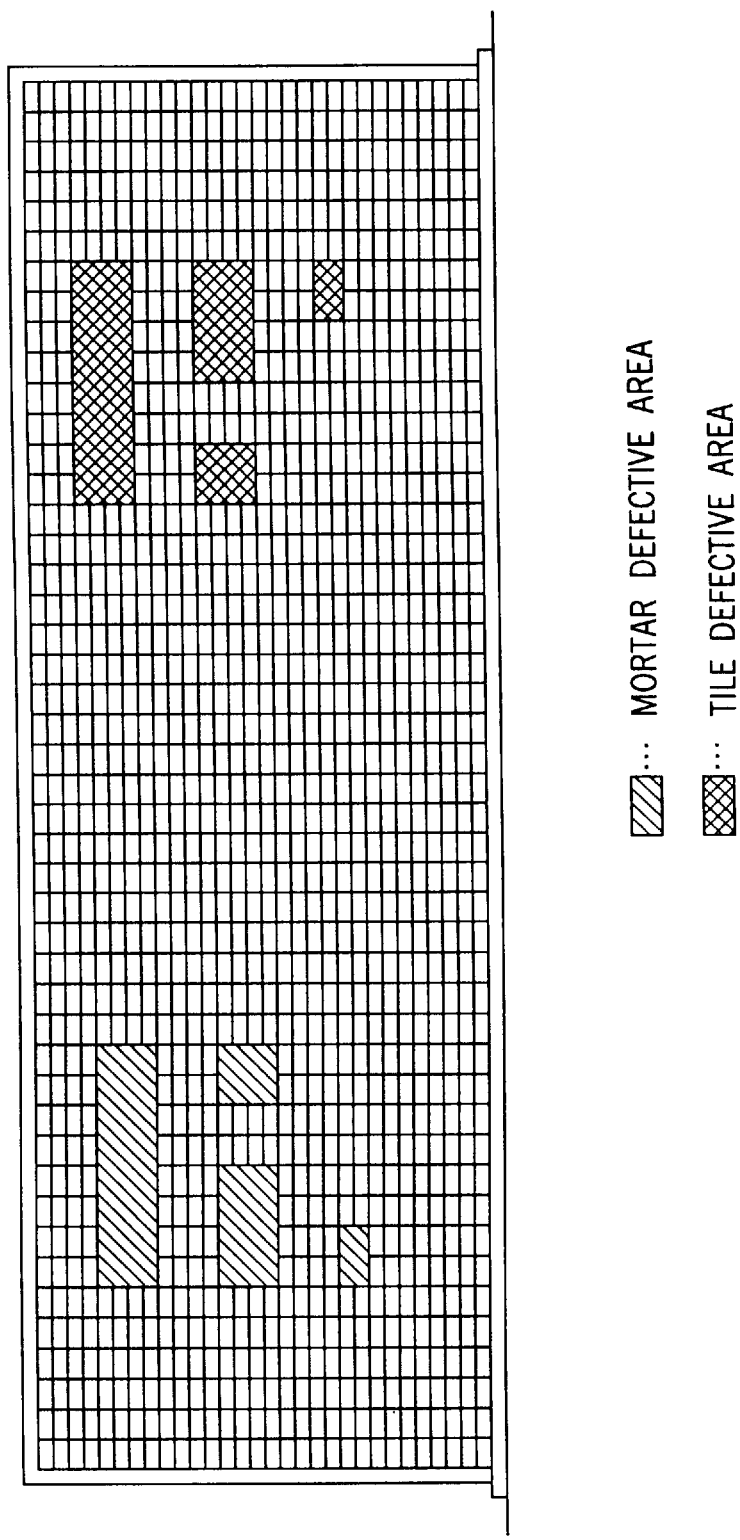

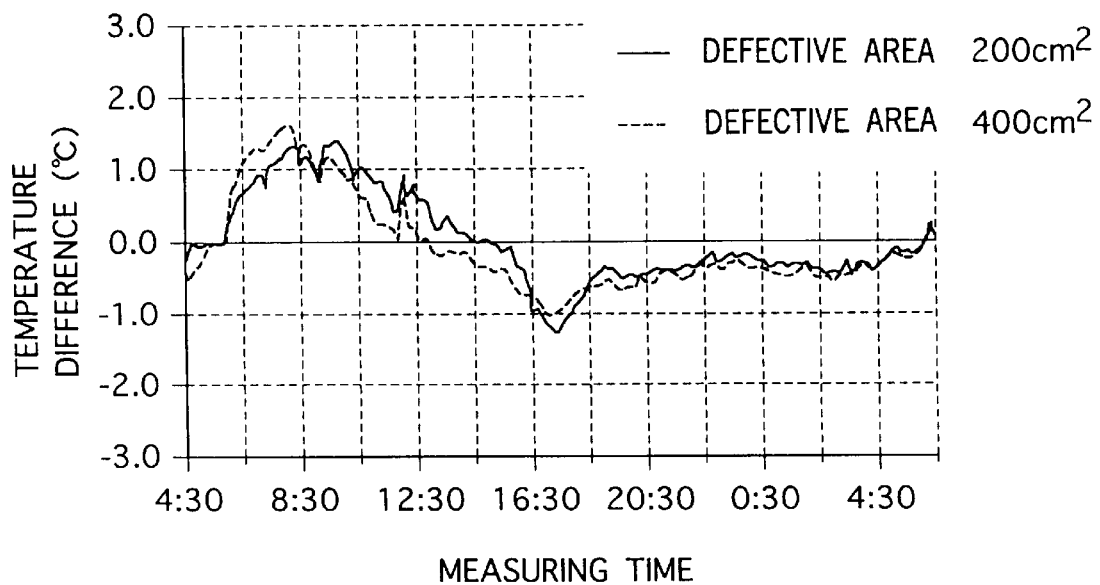
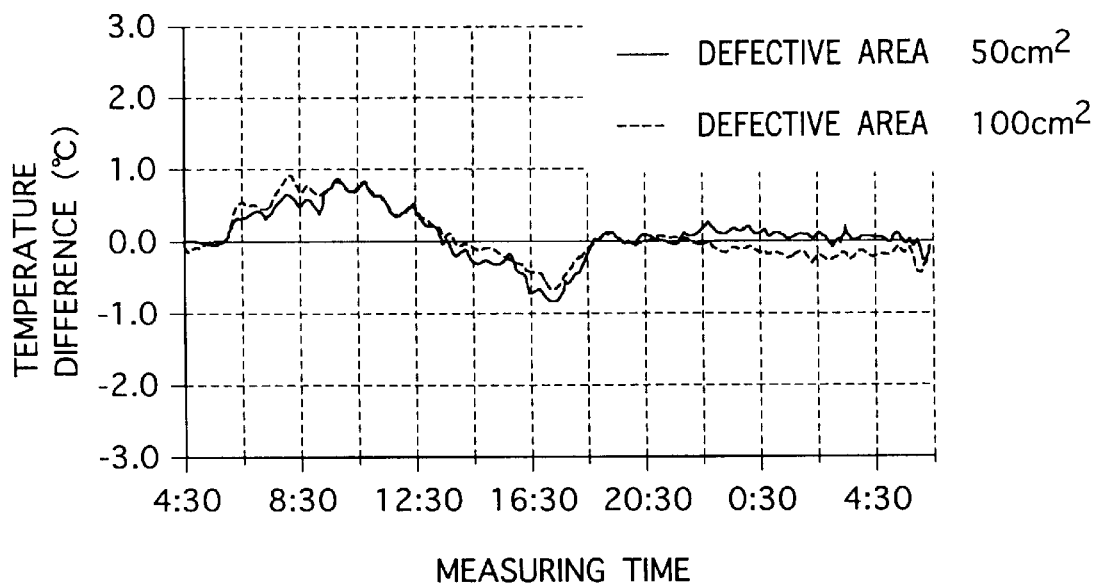

⊠ ... DEFECTIVE AREA

NON-DEFECTIVE AREA IN STEEL PLATE BONDED PORTION

WATER SUPPLY MAIN TUBE

METHOD OF DETECTING DEFECTS OF A STRUCTURE

BACKGROUND OF THE INVENTION

The present invention relates to a method for detecting defects in a structure.

Prior Art

Defects such as cracks in external walls, separation of mortar, or lifting of tiles take place in structures with the passage of an extended period of time. These defect may cause leakage of water or stripping of tiles. A tapping method has heretofore been known in which an operator taps the surface of a structure with, for example, a wooden hammer and determines the presence of defects by listening to the sound generated from the tapped surface.

However, this method is inferior in operation efficiency and reliability.

Hence, defect detecting methods which are excellent in operation efficiency and reliability have been demanded.

As one of these methods, there is a method in which the presence and/or position of a defect in a structure is determined by measuring the radiation energy from the structure surface by means of an infrared radiometer in order to identify the position.

Although this method is essentially excellent, various improvements in it have been proposed. Since the environmental conditions around actual structures are different, definitive conditions to determine whether a tile lifting defect occurs or not by detecting the radiation energy from the surface of the structure have not necessarily been made clear.

It is commonly practiced to detect defects in the daytime. In the daytime, the detection of the defect is liable to be affected by the sunlight exposure or shadow on the structure to be measured, or disturbances such as ambient temperature. Accordingly, incorrect determination is liable to be made due to these disturbances resulting in non-defective regions being stripped for repair.

The foregoing problem is more serious in that a determination of the defect is made based upon the results of one temperature measurement in the daytime so that the detection of a defect is more affected by disturbances.

Objective and concrete criteria to determine the level of the temperature to detect the defect in the structure surface have not been established. In practice, the distribution of the temperature on the structure surface is displayed on a CRT screen as an infrared image. An operator visually observes the difference in color of the infrared image displayed on the CRT screen to identify a region of the surface having a higher temperature than the other regions as a defective region. Such a qualitative determination based on the difference in color is not objective, by depends upon subjectivity of the operator. Different determinations are made by different operators, resulting in incorrect determinations.

Due to difference in season or time when the measurement is carried out, or difference in amount of sun light with which the structure is exposed or shadow of another structure, defective and non-defective regions may exhibit identical temperature distributions, or different defective or non-defective regions may exhibit different temperature distributions.

In such a case, it is very difficult to detect the presence or absence of defect only by measuring the temperature distribution on the structure surface by means of an infrared radiometer and by the operator visually observing the measurement results displayed on the CRT.

On the other hand, this detecting method using the infrared radiometer has not been used for detecting a defect of a steel plate reinforced concrete structure. The reason why this method has not been used for steel plate reinforced concrete structure is that it has been presumed that the temperature difference is so low that it is not possible to detect the defect even though the radiation energy from the surface is detected by the infrared radiometer because the size of the steel plate per se is so remarkably greater than that of the tile that sufficient energy is not actually provided from the steel reinforced structure.

BRIEF SUMMARY OF THE INVENTION

It is an object of the present invention to enhance the rate of the correct determination of a defect by positively detecting a defect of a structure.

It is another object of the present invention to detect a defect at a high accuracy based upon the distribution of the temperature on the surface of a structure, which is measured by an infrared radiometric thermometer.

It is a further object of the present invention to enhance the detection accuracy of a defect on the surface of a structure by making it possible to clearly determine the temperature difference between the defective regions of the surface and non-defective regions.

It is a further object of the present invention to enhance the accuracy of the detection of a defect of a steel plate reinforced structure by measuring the radiation energy from the structure surface by means of an infrared radiometer.

The above-mentioned objects are accomplished by providing a method of detecting a defect of an outdoor structure by measuring the radiation energy from the structure by means of an infrared radiometric thermometer, comprising the steps of: measuring the temperature of the surface of said structure by means of said infrared radiometric thermometer; and determining that there is a defect at a region of the surface if the temperature of the region differs by 0.3° C. or more and has a lower temperature than surrounding regions.

If the region of the surface having a temperature difference of 0.3° C. or more with surrounding regiongs is 200 cm$^2$ in an area a determination may be made that there is a defect at the region and if it is not higher than 200 cm$^2$, a determination may be made that there is no defect or the defect may be neglected.

Determination of the temperature of the surface of the structure may preferably be conducted by said infrared radiometric thermometer on 19:00 p.m. in a clear day when it is clear at least in the daytime to 4:30 a.m. in the next day.

Measuring of the temperature of the surface of the structure may be conducted at least once in the daytime and at least once in said period of time and determination of the defect may be made entirely based upon the results of both measurements.

The temperature of the surface of the structure may be detected in the daytime on the day in interest and a determination may be made that there is a defect at a region of the surface if the temperature difference of the region between the temperatures which are measured in the daytime and in the night is +0.3° C. or more in the daytime and is −0.3° C. or more in the night.

The temperature of the surface of the structure may be detected by means of said infrared radiometric thermometer in the daytime and night to obtain the temperature distributions at the respective times, and a differential temperature distribution may be obtained by performing an differential operation between these temperature distributions, and a defect of the structure may be detected based upon the differential temperature distribution.

An integrated temperature distribution may be obtained by integrating said differential temperature distribution for time and in which the defect of the structure is detected based upon the integrated temperature distribution.

Measurement of the temperature may be by means of the infrared radiometric thermometer at a plurality of different times; and a determination is made that there is a defect at a region of the surface if the regions has a temperature difference of 0.3° C. or more.

When said structure is reinforced with steel plates which are integral with a concrete slab of the surface thereof, a determination may be made that there is a defect at a region of the surface having a temperature difference of 0.3° C. or more, in comparison with that of the surrounding regions if the area of the region is 400 cm$^2$ or more and a determination is made that there is no defect or the defect is neglected if the region is not more than 400 cm$^2$ in area.

In the present invention, a determination of whether or not a lifting defect is present is not based upon the absolute level of the temperature, but based upon the temperature difference between the region of the surface to be measured and the surrounding regions. If the determination is made based upon the level of absolute temperature or the temperature distribution which is obtained from the detected thermal image, determination error due to personal difference is liable to occur. Since the determination is based upon the temperature difference which is obtained by a signal processing in accordance with the present invention, the determination can be made objective.

Various disturbances affect a captured thermal image signal even though the temperature difference between the region of interest and the surrounding region is high. Accordingly, the present invention makes a determination that there is a defect at a region of a surface if the area is not less than 200 cm$^2$ when the region has a temperature difference of 0.3° C. or more in comparison with another region. Conversely, the present invention makes determination that there is no defect at a region having a temperature difference of not less than 0.3° C. if the area is not larger than 200 cm$^2$, or it neglects the defect.

In case in which a determination whether there is a lifting defect is made with reference to a temperature difference between a region of in interest and the surrounding regions, the temperature difference is often not less than 0.3° C. due to disturbances if the region of in interest is not less than 200 cm$^2$. If a determination that there is a defect in all regions having a temperature difference of 0.3° C. or more is equally made, non-defective regions may be determined to be defective regions. On the other hand, it may be presumed from the empirical view of point that it is a rare case in which only one tile is lifted while all the surrounding tiles are non-defective and that surrounding tiles are also lifted around the lifted tile. It is practical and no problematic to determine that there is no defect if the region of interest having a temperature difference of 0.3° C. or more is not less than 200 cm$^2$.

The present inventors obtained the following findings from the various experiments which will be described.

(1) In the daytime, the temperature is largely affected by disturbances such as the changes in sunlight exposure, presence of shadow on the outdoor building to be measured, or the ambient temperature. In other words, the sunlight largely changes in a relatively short period of time on each of east, west, south and north sides as shown in FIG. 5. The temperature is also affected by the position of a cloud or the shadow of other buildings. Furthermore, the changes in ambient temperature are large as shown in FIG. 6 (the temperature is temporarily lowered by the influence of falling rain and wind).

As a result, the surface temperature of the outdoor structure delicately changes in a short period of time. The temperature difference between the defective region and non-defective region becomes large due to large changes of the surface temperature with the lapse of time. Therefore, in the daytime disturbances such as sunlight exposure may cause incorrect determination of defect.

(2) Accordingly, a defect can be properly detected without being influenced by the disturbances if the temperature is measured in a period of time 19:00 in the day when it is clear at least in the daytime to 4:30 in the next day.

In the daytime, the temperature on the surface of a structure is elevated due to sun light exposure. Part of the solar energy which is incident upon the surface is reflected thereon while the other is absorbed by the structure. The absorbed thermal energy is transmitted in a depth direction. The temperature on the surface of the structure is determined depending upon the relation between the thermal energy and the heat transmission rate. If there is a defect such as lifting of tiles, heat transmission is hindered at the lifted region so that transmission of the absorbed thermal energy is delayed. The temperature on the surface of the defected region becomes higher than that of another non-defective region.

In the night, a reversed heat transmission in an opposite direction occurs in which the heat energy which is absorbed by the structure dissipates to an atmosphere having a lower temperature. Accordingly, a reversal phenomenon occurs in which the temperature on the surface of the structure is lower than that inside of the structure. "Reversal phenomenon of the temperature difference" in which the defective region is lower in temperature than non-defective region occurs under this reversed phenomenon.

The difference between the temperature differences between the defective and non-defective regions of the surface in the daytime and the night is considered. In the night there are little disturbances such as sunlight exposure or the presence of shadows. The temperature difference depends on the rate at which the thermal energy which is absorbed by the structure is dissipated to the atmosphere having a lower temperature. This is due to the fact that the changes in temperature difference with lapse of time is low under the above-mentioned "reversal phenomenon of the temperature difference."

As will be described by the embodiments, the rate of correct determination of the defect in the night is higher than that in the daytime.

An error is liable to occur in the defect determination since the thermal energy which is absorbed by the structure is low in a rainy or cloudy day and the amount of thermal energy dissipated to the atmosphere is low. An error in the defect determination may be caused by the determination that there is a defect at a region having a temperature difference of 0.3° C. or more between the adjacent unit regions.

(3) A defect has conventionally been determined based on the result of measurement which was conducted only one time.

In contrast to this, it is preferable to measure the temperature in the night in accordance with the present invention as mentioned above. In order to enhance the accuracy of the correct defect determination, it is more preferable that the measurements are conducted plural times in the night for totally determining the defect. As is apparent from the above-mentioned sequential changes in temperature, the changes in temperature difference in the daytime is larger than that in the night. Determination of the defect can be totally conducted based upon both results of the measurements which were conducted at least once in the daytime and at least once in the night.

It is preferable to determine that there is a defect at a region if the region has a temperature difference between the surface temperatures of the structure in the daytime and night of +0.3° C. or more in the daytime and of −0.3° C. or more in the night.

Further, in the present invention, in view of the above-mentioned "reversal phenomenon of temperature difference" the radiation energy is detected by the infrared radiometer in the daytime and night, to obtain the distributions of the temperature on the surface of the structure at the respective times. A differential temperature distribution is obtained by conducting a differential operation between both temperature distributions. Since "reversal phenomenon" occurs between the daytime and night, the temperature difference between the defective and non-defective regions is enhanced by obtaining the differential temperature distribution, so that it become more clear. It becomes easier for operator to detect the defect when the visually observes the differential temperature distribution displayed on the CRT.

The temperature difference between the defective and non-defective regions can be enhanced by integrating the differential temperature distribution for time. It thus becomes easier to detect the defect.

On the other hand, in the present invention, in order to detect a defect of a structure which is reinforced with steel plates which are integral therewith, the radiation energy from the reinforced surface of the structure is measured by means of the infrared radiometric thermometer to detect the defect based upon a signal from the thermometer.

This kind of method has been used for detecting a defect of an external tile wall face. In such a conventional detection method, the distribution of the temperature on the structure surface is displayed on a CRT as an infrared image and an operator visually observes the image on the CRT to determine the level of the temperature to make a decision relating to the defect. This determination is not objective, but is based upon operator's subjectivity. Determinations are different among persons wrong detection of the defect is liable to be made.

In contrast to this, the detection method of the present invention is not based upon the operator's subjectivity so that it is applicable to steel plate reinforced structures.

"Reversal phenomenon of the temperature difference" occurs even in the structure which is reinforced with steel plates on the surface thereof. In other words, the temperature of the reinforcing steel plate is elevated on exposure to sun light in the daytime. Part of the solar energy which is incident upon the surface is reflected thereon while the other is absorbed by the structure. The absorbed thermal energy is transmitted in a depth direction of the concrete slab. The heat transmission is hindered by a defect such as an air gap which is formed due to insufficient filler and separation of steel plate due to vibration. The transmission of the absorbed thermal energy is delayed, so that the temperature on the surface of the defective region is higher than that of the non-defective region.

In the night, heat transmission in a reversed direction occurs in which the thermal energy which is absorbed by the structure is dissipated to atmosphere having a lower temperature. Accordingly, reversal phenomenon of the temperature difference occurs, similarly to a structure having no reinforcing steel plate, which has a lower temperature on the surface thereof, and a higher temperature inside thereof. Under this condition, reversal phenomenon of the temperature difference in which the defective region is lower in temperature than non-defective region occurs. It is deemed that the reason of this phenomenon is that it takes longer time for the non-defective region to be cooled since heat transmission is conducted via the non-defective region while the steel plate surface at the defective region is cooled in a short period of time and thereafter heat transmission is hardly conducted.

Therefore, the present invention is preferably applicable to steel plate reinforced structures. In the case in which the size of the steel plate is remarkably larger than that of the tile and enough energy is not provided to the steel plate reinforced structure, the temperature difference is small even if the radiation energy from its surface is detected by the infrared radiometer. In view of this, it may be determined that there is a defect at a region of the surface if the area is 400 $cm^2$ or more.

BRIEF DESCRIPTION OF THE SEVERAL VIEWS OF THE DRAWINGS

FIG. 2 is a schematic view showing an example of a wall of a structure to be measured;

FIGS. 3 to 34 are graphs showing the results of the experiments of the present invention;

DETAILED DESCRIPTION OF THE INVENTION

Now, modes of the preferred embodiments of the present invention will be described in detail.

The basic method of detecting a defect of the present invention is conducted as follows; An infrared radiometric thermometer (thermal image sensor) is provided to facing the surface of the structure to be measured. The infrared radiation energy from the surface is detected. The detected signal is fed to an image analyzing device in which the temperature in the image range and the temperature distribution is obtained. Based on this information, it is determined that there is a defect at a region of the surface having a temperature difference of 0.3° C. or more and has a lower temperature. To this end, a contour map representing temperature difference is prepared based upon the measured temperatures at respective regions of the surface.

In this case, as a reference temperature which is a reference for a temperature difference, an average temperature in a given imaged region at a measuring time is ##adopted, or a minimum temperature (excluding a temperature which is remarkably different from the average temperature) in a group of unit areas which are segmented from an imaged region at a measuring time may be adopted, or the temperature at a region of the surface where the temperature does not change over a given length in a graph showing the temperature difference, since the area of the defective portion is smaller than that of the non-defective area, may be adopted. These adopted reference temperatures are not substantially different.

On the other hand, it is necessary to obtain the correlation between the area in the contour map and the actually measured surface (reinforcing steel plate surface) since they are relevant in the contour map of the temperature difference. Hence, in practice, it is possible to determine whether or not the region having a temperature difference of 0.3° C. or more is not less than 200 $cm^2$ of the measured area by measuring the distance between the position of the infrared radiometric thermometer and the measured steel plate surface by means of measuring instrument or by making the area of the current image proportional to the area of the steel plate by also considering the angle of the depression or elevation if the position of the infrared radiometric thermometer has been known on the map. In this case, the magnification of the lens used during the detection should be also considered.

Thus, if the region of the detected surface is 200 $cm^2$ or more in area, it is determined that there is a defect in this region. If it is not greater than 200 $cm^2$, it is determined that there is no defect or it is neglected. The limitation of the area of the measured surface and the temperature difference is determined by the following experiment which is described in detail.

EXPERIMENT 1

Figure 1:
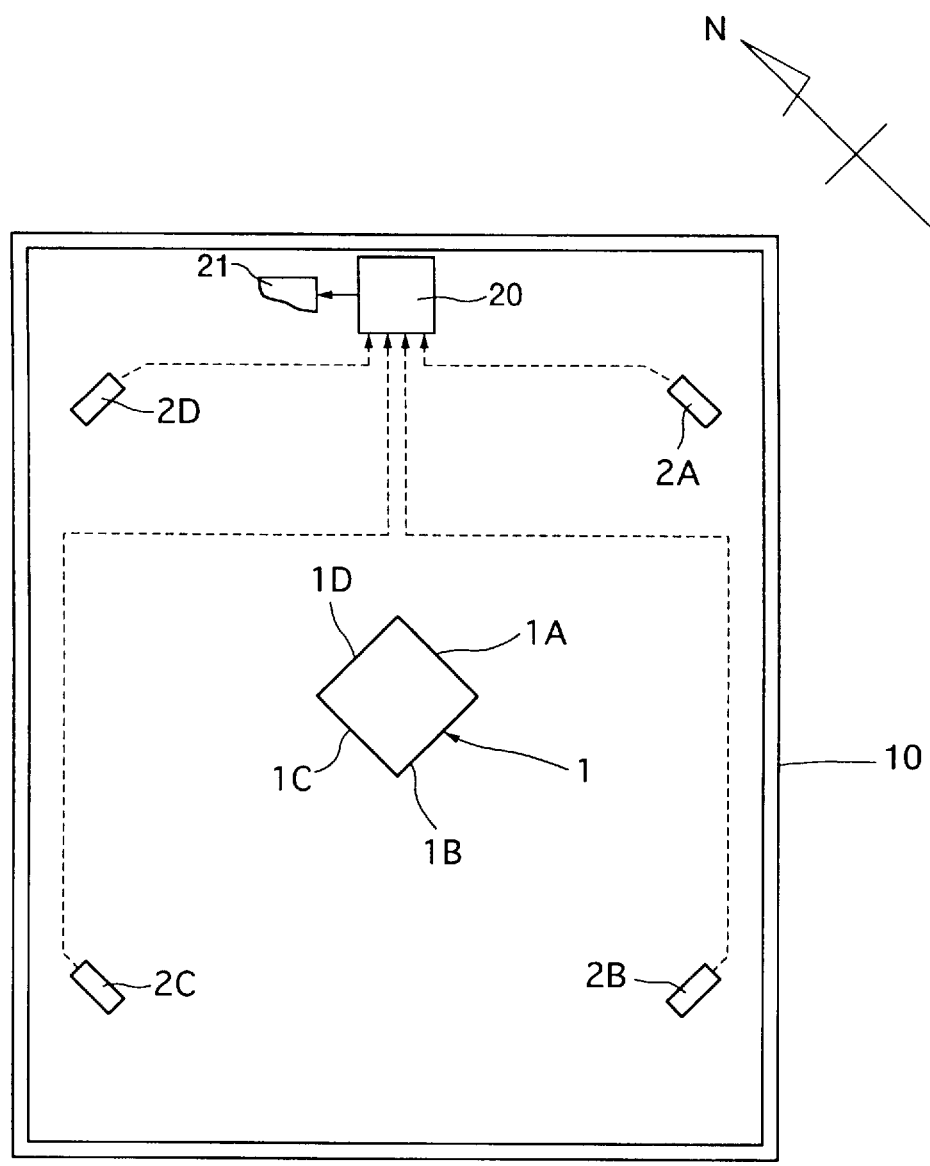
FIG. 1 is a schematic view showing a system in which the present invention is embodied.

A model structure 1 with sides, each having a width of 5 m and a height of 1.8 m on which new small tiles are applied is built on the roof of building existing at a rural city as shown in FIG. 1. Tiles are bonded to the external walls 1A to 1D by means of a mortar layer. A simulated defect (half of which is a tile separated defect having a depth of 0.6 cm, the other half of which is a mortar lifting defect having a depth of 2.6 cm) was intentionally formed on each of the east, south west and north sides external walls 1A, 1B, 1C and 1D, respectively so that it occupies about 7% of each side. Each of the tile separated defect portion and mortar separated portion comprises an area of 8 tiles, an area of 4 tiles, an area of 2 tiles and an area of one tile in order to determine whether there is a temperature difference due to difference in area of the defective region. An area of 7% is an average value which is found by actual tile defect investigation.

In order to detect the defect of the external walls, infrared radiometric thermometers (thermal image sensors) which face the external walls are placed on the roof.

Signals from the thermometer 2A to 2D are input to an image analyzing device 20. The analyzed result is displayed on a CRT display 21 or is recorded on a floppy disk and the like.

In the thus formed system, the infrared radiation energy from each of the external walls 1A to 1D is detected by the infrared radiation thermometer 2A to 2D. An average temperature of each unit area is obtained by dividing the measured area and presence or absence of a detect is determined based upon the temperature difference between adjacent unit areas.

In the experiment, measurements were conducted by means of an infrared radiometric thermometer successively every 10 minutes for about 25 hours since the sunrise on a clear day in spring.

The changes in the temperature difference between the mortar lifting defect region and non-defective region, corresponding to 8 tiles (area of 400 $cm^2$ and so forth) and 4 tiles (area of 200 $cm^2$ and so forth) on the east side are shown in FIG. 3. The changes in the temperature difference between the mortar lifting defect region and non-defective region, corresponding to two tiles (area of 100 $cm^2$ and so forth) and one tile (area of 50 $cm^2$ and so forth) are shown in FIG. 4. The change in the sunlight exposure and ambient temperature on each side are shown in FIGS. 5 and 6 respectively.

Referring to the changes in the temperature difference between the defective region and non-defective region as shown in FIGS. 3 and 4, the temperature difference between the defective region and non-defective region is 0.3° C. or more in most times excepting the period of time (13:00 to 15:00, 4:30 to 6:30) in which the above-mentioned "reversal phenomenon of the temperature difference" occurs when the defective area is 400 $cm^2$ and 200 $cm^2$ as shown in FIG. 3. In contrast to this, the temperature difference is not more than 0.3° C. excepting the period of time before and after some periods of time (6:30 to 12:00, 15:30 to 18:30) in the daytime when the defective area is 100 $cm^2$ and 50 $cm^2$ as shown in FIG. 4.

Figure 5:
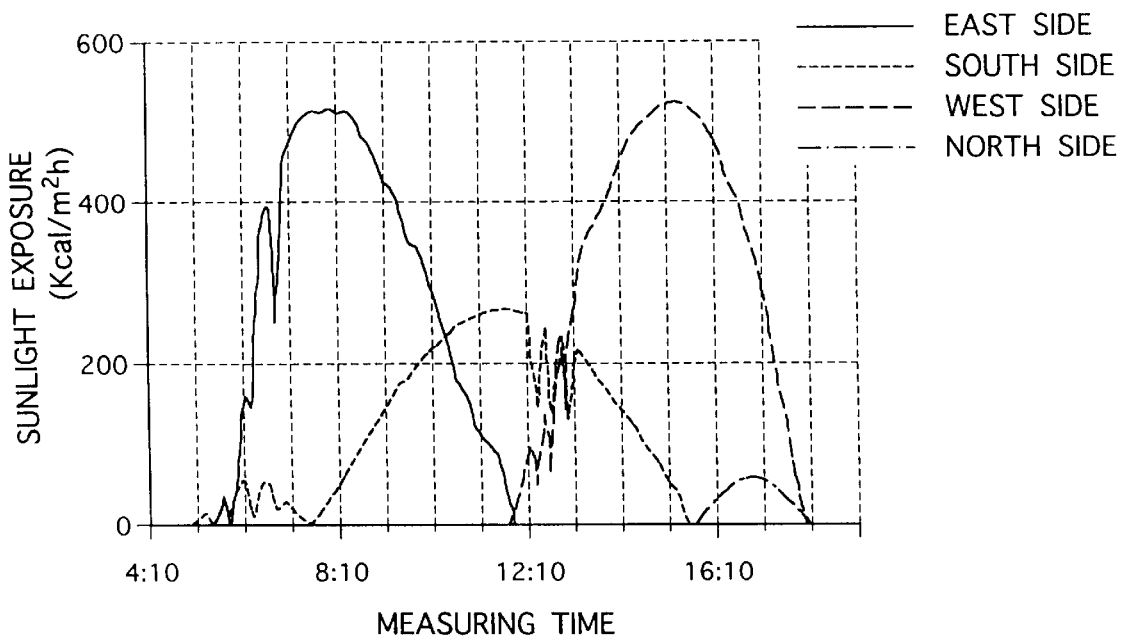
Figure 6:
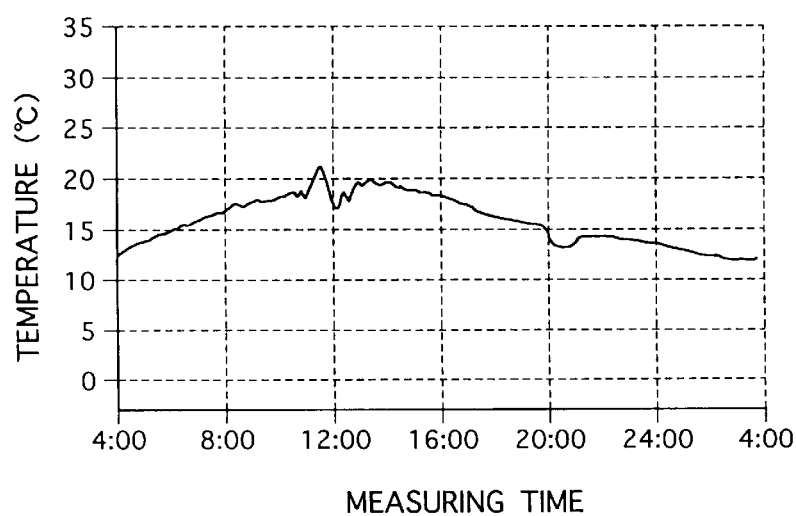

It is preferable that defect detection be performed in the night since there is a risk of wrong detection of the defect due to the fact that the sunlight exposure on the east side is high in the morning as shown in FIG. 5 and the ambient temperature is unstable in the daytime as shown in FIG. 6. However, the temperature difference between the defective and non-defective regions is hardly 0.3° C. or more in the night at the area corresponding to 2 tiles and one tile.

It is found from the above-mentioned results that a minimum area at which the mortar defect can be detected at a high accuracy is 200 $cm^2$. Accordingly, it is found that in order to detect the mortar defect on the east side in spring, it suffices to divide the region to be detected into 200 $cm^2$ areas.

Figure 7:
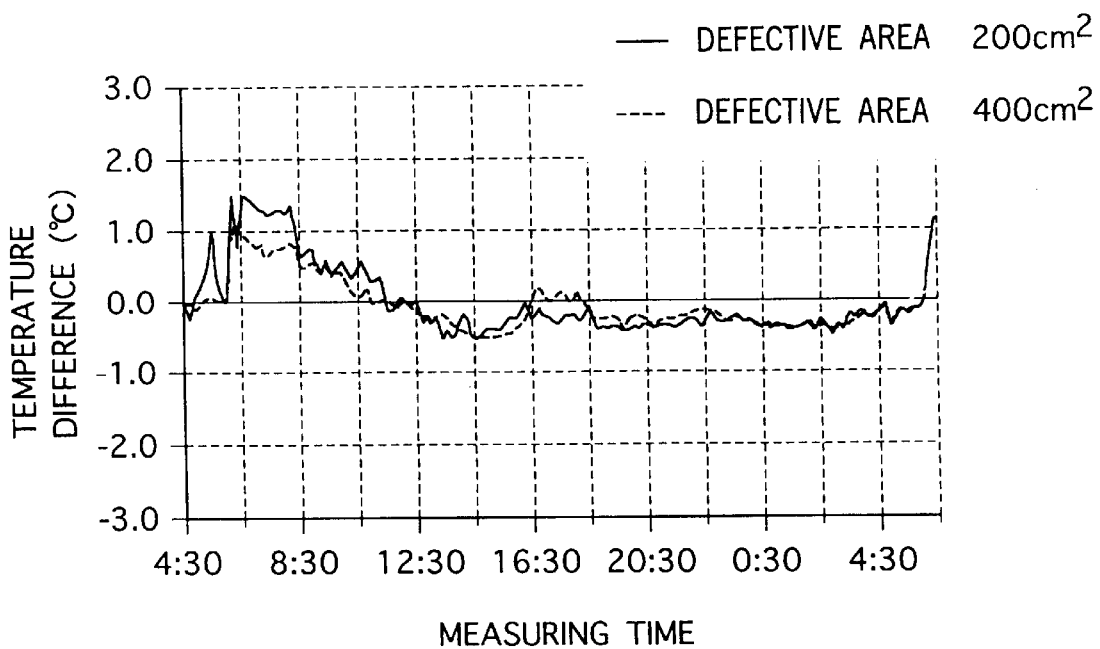

The changes in the temperature difference between the mortar lifting defect region and non-defective region, corresponding to 8 tiles (area of 400 $cm^2$ and so forth) and 4 tiles (area of 200 $cm^2$ and so forth) on the east side are shown in FIG. 7. The changes in the temperature difference between the mortar lifting defective region and non-defective region, corresponding to two tiles (area of 100 $cm^2$ and so forth) and one tile (area of 50 $cm^2$ and so forth) are shown in FIG. 8.

Figure 8:
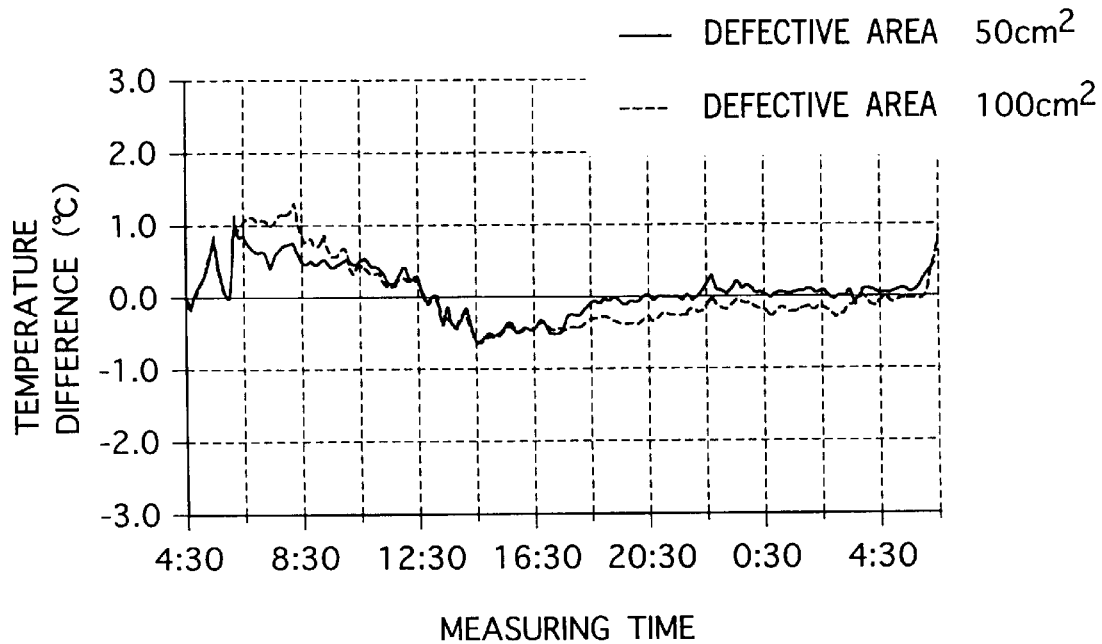

Referring to the changes in the temperature difference between the defective region and non-defective region as shown in FIGS. 7 and 8, the temperature difference between the defective region and non-defective region is 0.3° C. or more in most times excepting the period of time (13:00 to 15:00, 4:30 to 6:30) in which the above-mentioned "reversal phenomenon of the temperature difference" occurs when the defective area is 400 cm² and 200 cm² as shown in FIG. 7. In contrast to this, the temperature difference is not more than 0.3° C. excepting the period of time before and after some periods of time (6:30 to 12:00, 15:30 to 18:30) in the daytime when the defective area is 100 cm² and 50 cm² as shown in FIG. 8.

It is preferable that defect detection be performed in the night in order to avoid an influence by the sunlight exposure and the ambient temperature as is similar to the detection of mortar lifting defect. However, the temperature difference between the defective and non-defective regions is hardly 0.3° C. or more in the night at the area corresponding to 2 tiles and one tile.

It is found from the above-mentioned results that a minimum area at which the tile defect can be detected at a high accuracy is 200 cm². Accordingly, it is found that in order to detect the mortar defect on the east side in spring, it suffices to divide the region to be detected into 200 cm² areas.

Figure 9:
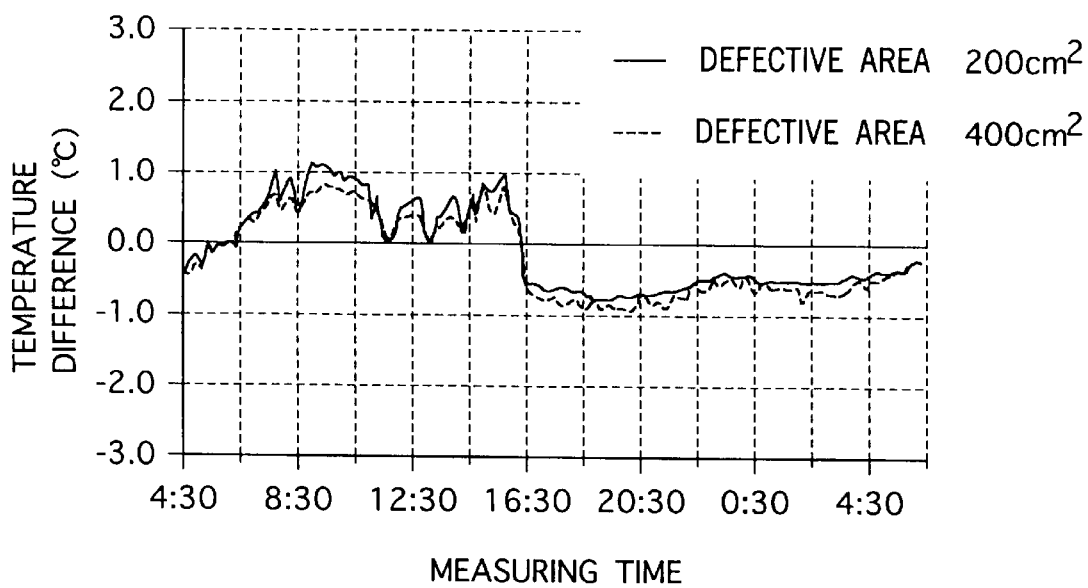
Figure 10:
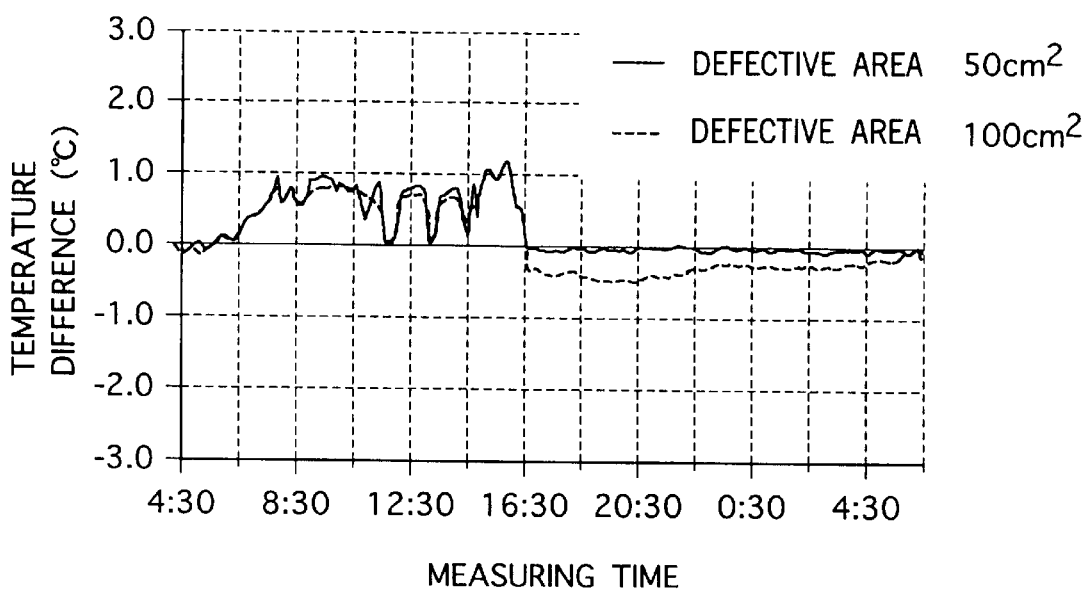
Figure 11:
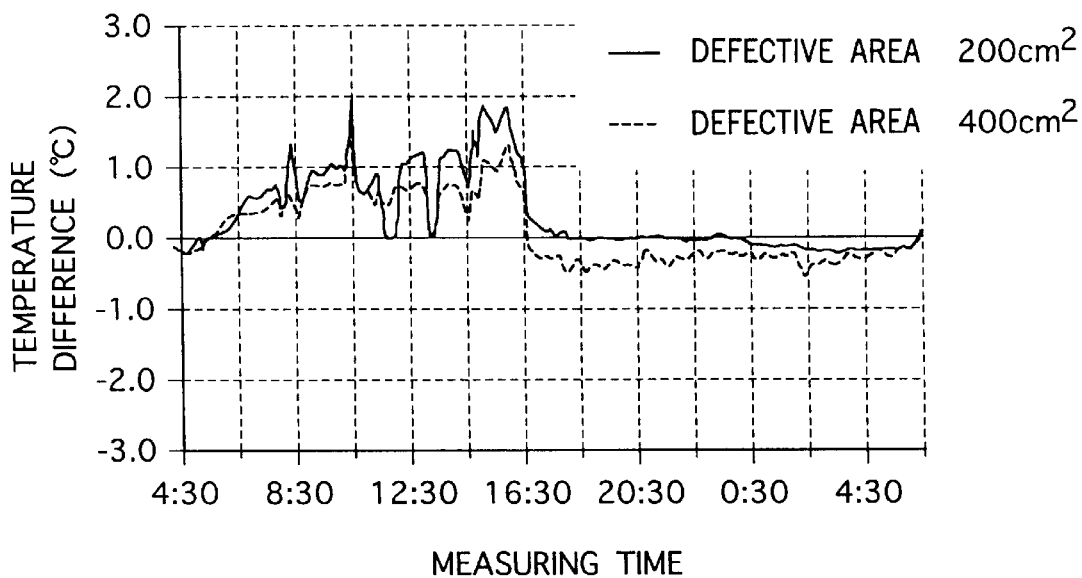
Figure 12:
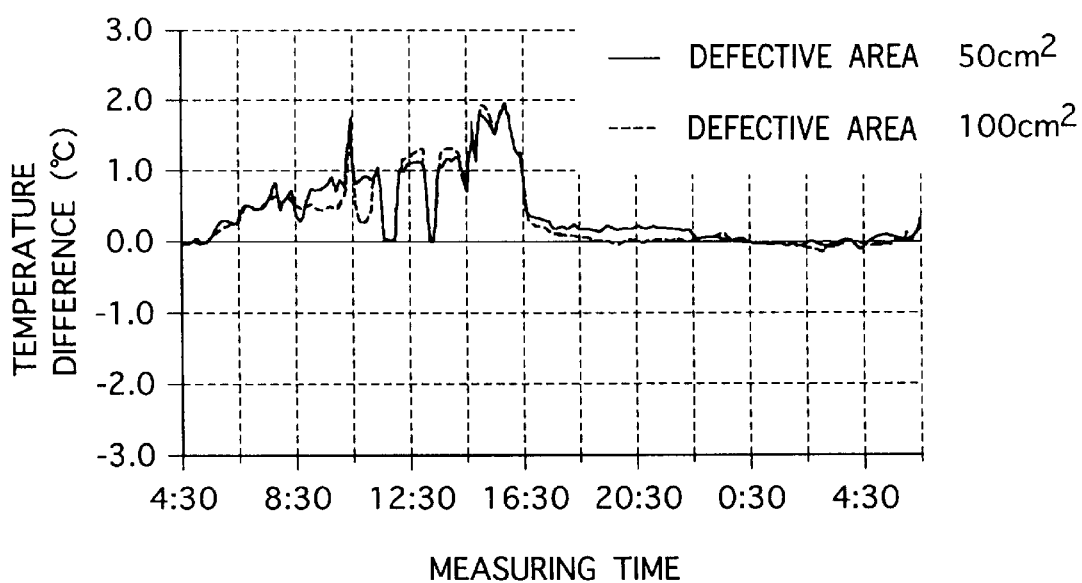
Figure 13:
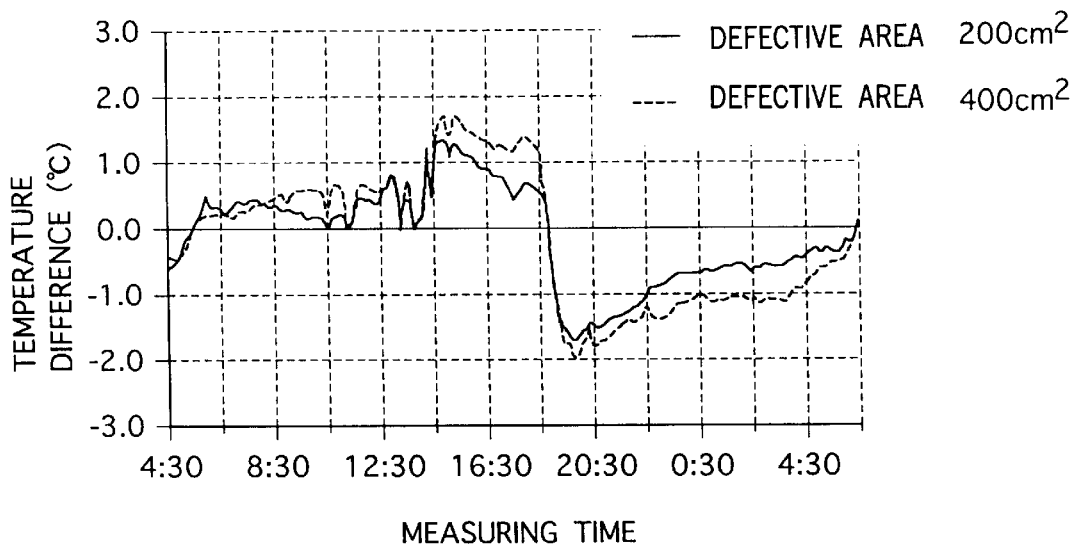
Figure 14:
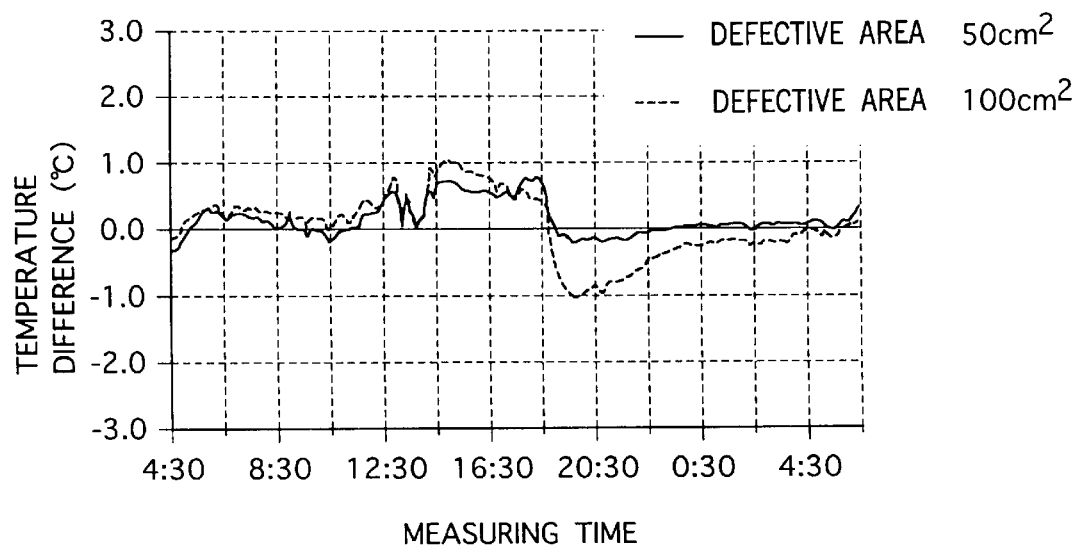
Figure 15:
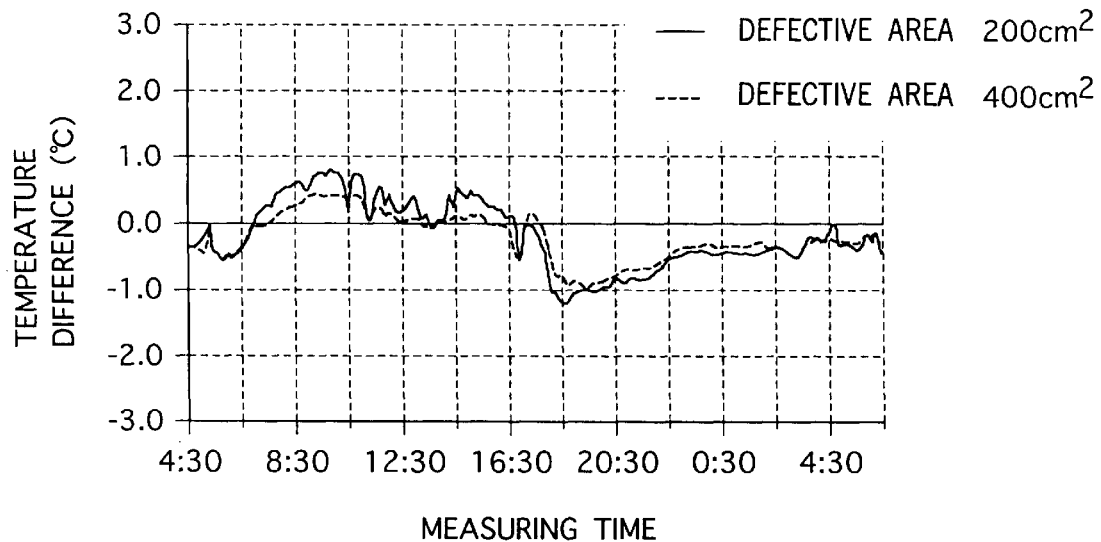
Figure 16:
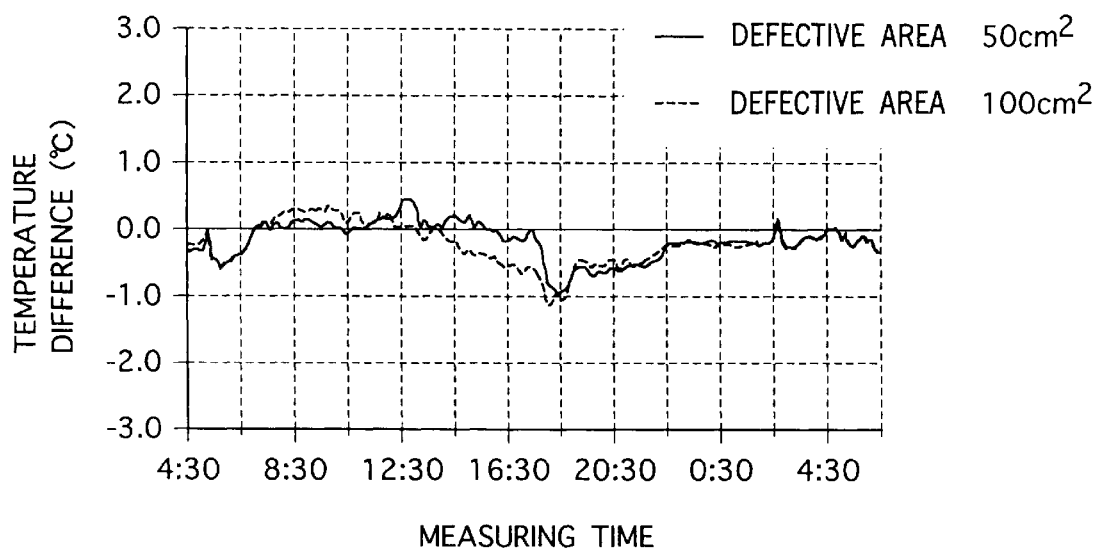
Figure 17:
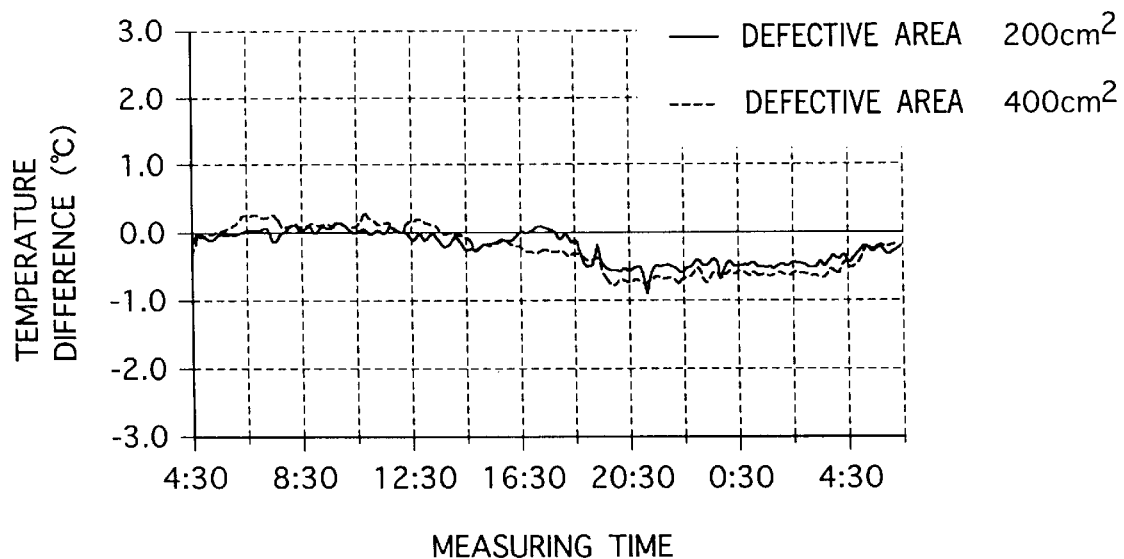
Figure 18:
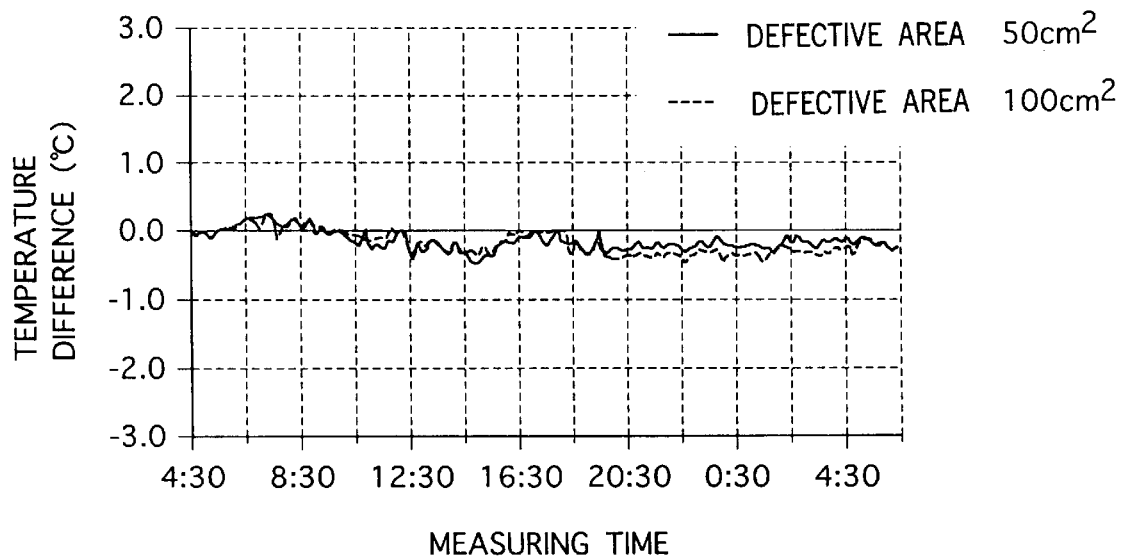
Figure 19:
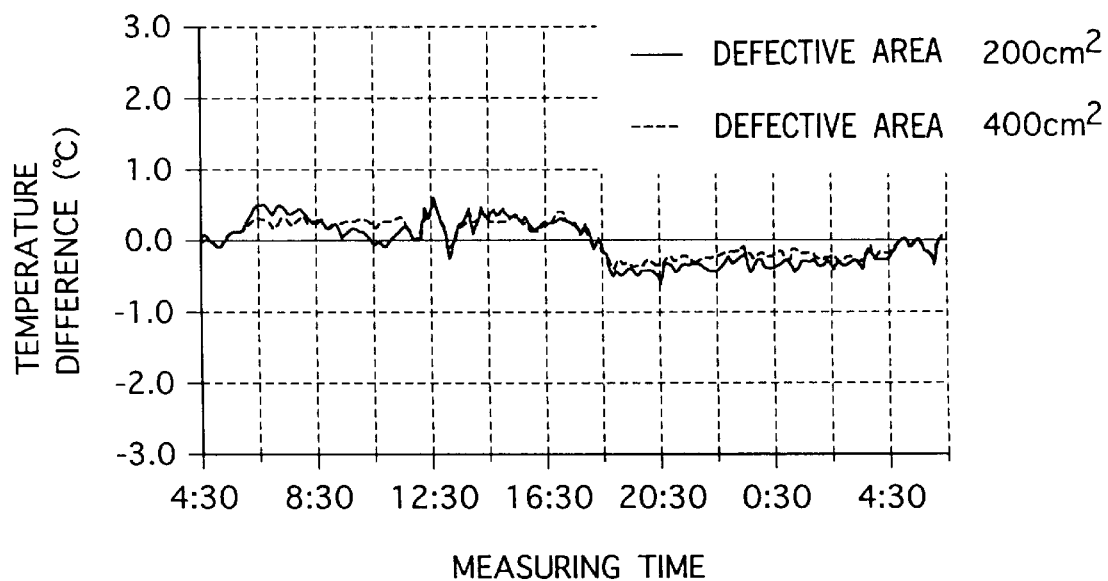
Figure 20:
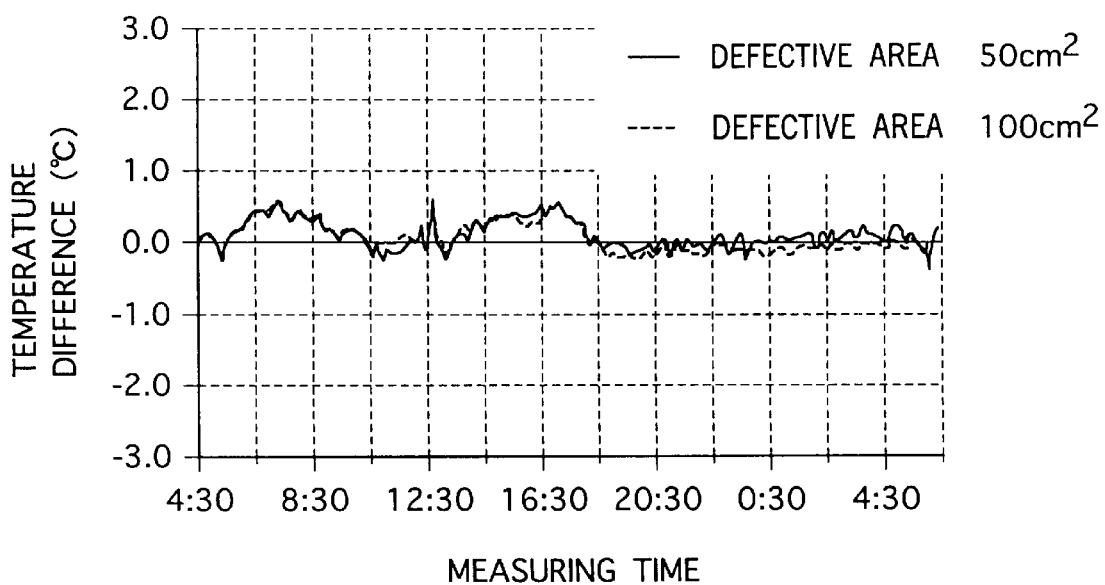

The foregoing results were obtained by the experiment on the east side. Similar experiments were conducted on the other south, west and north sides. The changes in the temperature difference between the mortar lifting defective region and non-defective regions on south side with the lapse of time are shown in FIGS. 9 and 10. The changes in the temperature difference between the tile lifting defective region and non-defective regions on south side with the lapse of time are shown in FIGS. 11 and 12. The changes in the temperature difference between the mortar lifting defective region and non-defective regions on west side with the lapse of time are shown in FIGS. 13 and 14. The changes in the temperature difference between the tile lifting defective region and non-defective regions on the west side with the lapse of time are shown in FIGS. 15 and 16. The changes in the temperature difference between the mortar lifting defective region and non-defective regions on north side with the lapse of time are shown in FIGS. 17 and 18. The changes in the temperature difference between the tile lifting defective region and non-defective regions on north side with the lapse of time are shown in FIGS. 19 and 20.

These results shown in each of Figs. was considered as is similar to the case in which a minimum area is determined to enable a defect to be detected on the east side at a high accuracy. Explanation of the detailed procedure of consideration will be omitted since they are similar to each other. As a result, the minimum area at which the mortar lifting defect and tile lifting defect can be detected at a high accuracy is as follows:

100 cm² for the mortar lifting defect on the south side;
100 cm² for the tile lifting defect on the south side;
100 cm² for the mortar lifting defect on the west side;
100 cm² for the tile lifting defect on the west side;
50 cm² for the mortar lifting defect on the north side;
200 cm² for the tile lifting defect on the north side.

Figure 21:
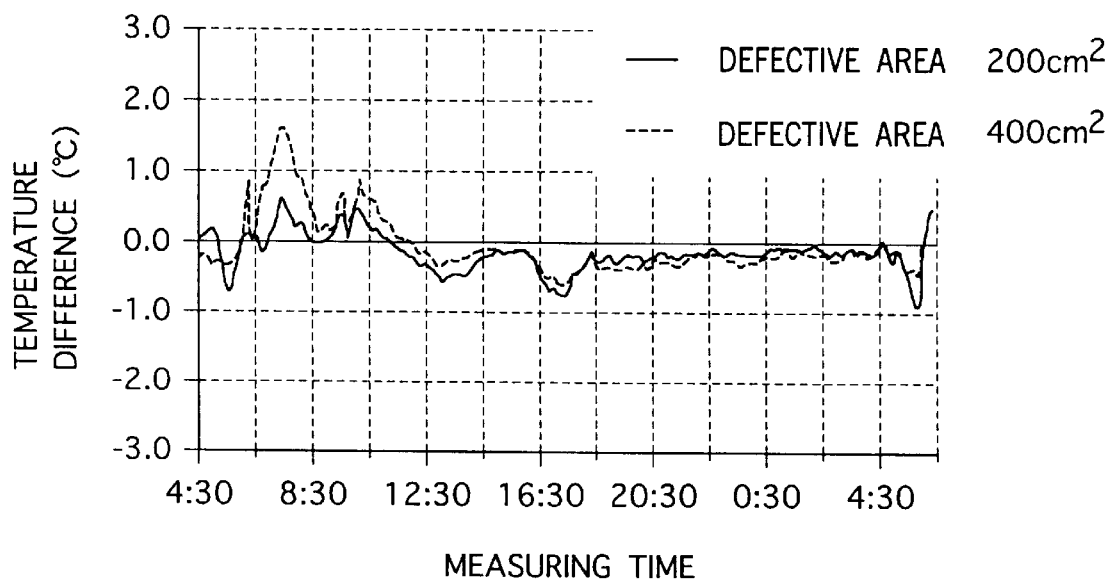
Figure 22:
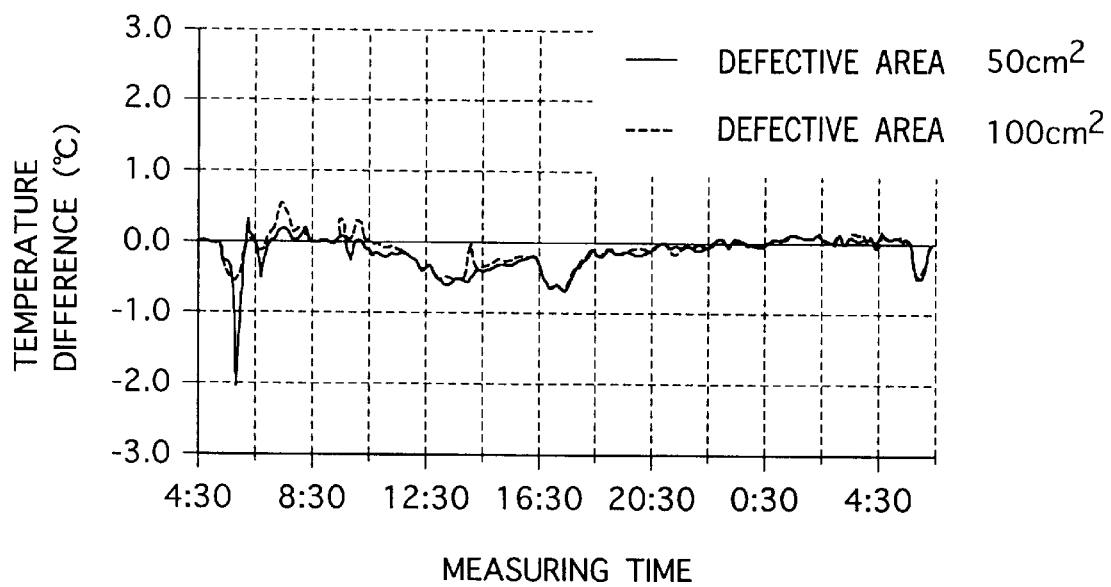
Figure 23:
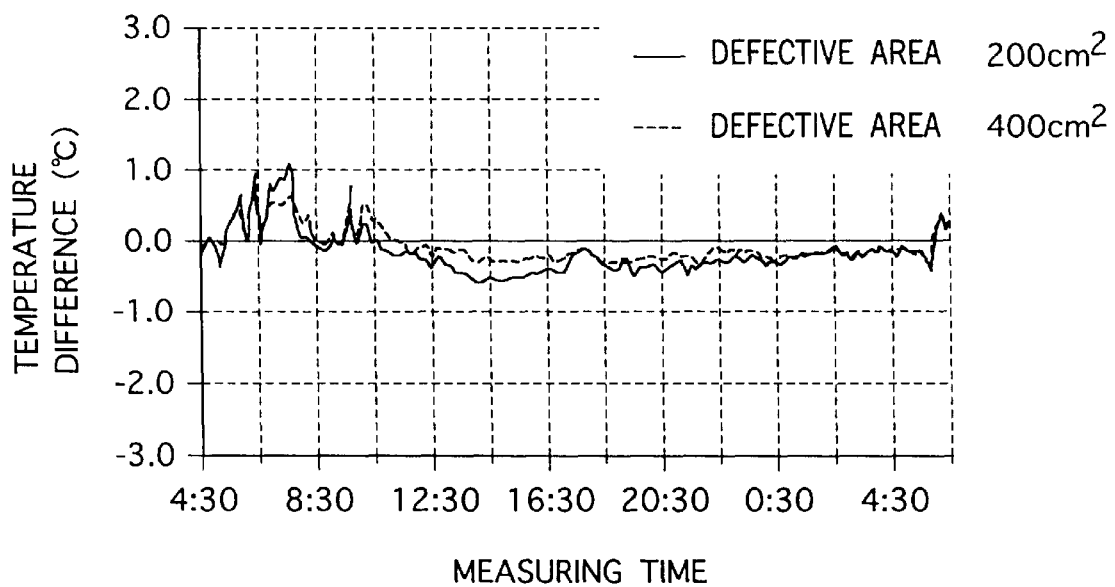
Figure 24:
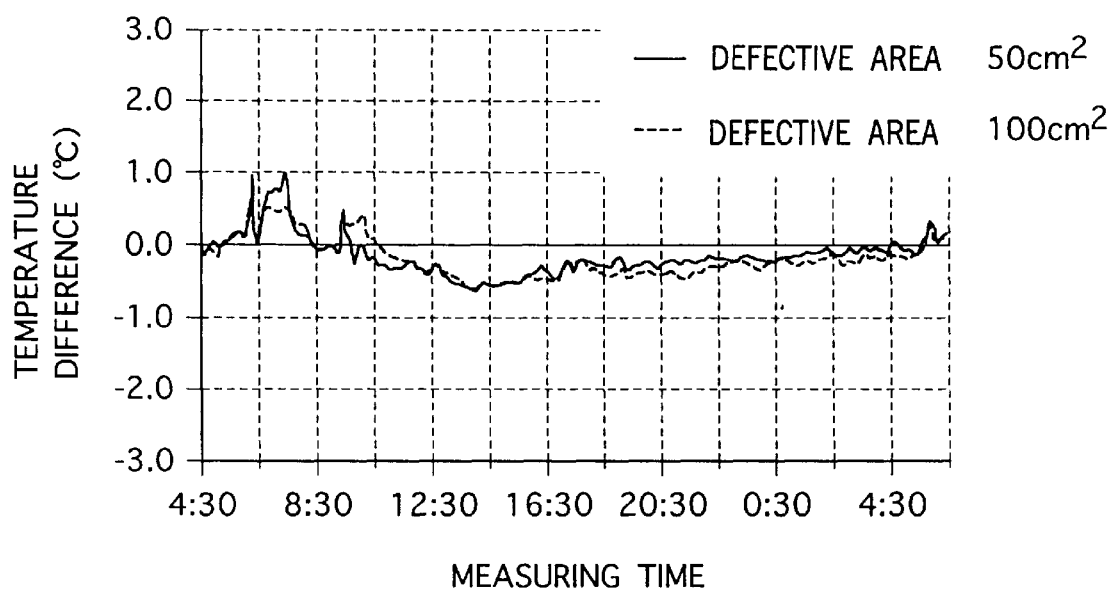

The foregoing results were obtained by the experiments which were conducted in spring. Similar experiments were carried out when it was summer. The temperature differences with the lapse of time between the mortar lifting defect and the non-defective regions on the east side in summer are illustrated in FIGS. 21 and 22. The temperature differences with the lapse of time between the tile lifting defect and non-defect regions are illustrated in FIGS. 23 and 24.

The results in summer were considered similar to the case in spring. Although the considering process is not described in detail, it is found from the results that the minimum areas at which the mortar and tile lifting defect on the east side in summer can be detected at a high accuracy are 200 cm² and 50 cm², respectively.

Experiments were conducted on south, west and north sides similarly to that in spring. Similar experiments were conducted on east, south, west and north sides in autumn and winter to determine the minimum area at which the mortar and tile lifting defects can be detected at a high accuracy.

The minimum areas at which the mortar and tile lifting defects can be detected at a high accuracy in each season in each detection direction are shown in Tables 1 and 2, respectively.

TABLE 1

| Seasons | Detection Direction | Detectable min. area number of mortar units (area) |
| --- | --- | --- |
| spring | east | 4 (200 cm²) |
| | south | 2 (100 cm²) |
| | west | 2 (100 cm²) |
| | north | 1 (50 cm²) |
| summer | east | 4 (200 cm²) |
| | south | 2 (100 cm²) |
| | west | 2 (100 cm²) |
| | north | 4 (200 cm²) |
| autumn | east | 2 (100 cm²) |
| | south | 4 (200 cm²) |
| | west | 4 (200 cm²) |
| | north | 1 (50 cm²) |
| winter | east | 1 (50 cm²) |
| | south | 1 (50 cm²) |
| | west | 1 (50 cm²) |
| | north | 2 (100 cm²) |

TABLE 2

| Seasons | Detection Direction | Detectable min. area number of mortar units (area) |
| --- | --- | --- |
| spring | east | 4 (200 cm²) |
| | south | 2 (100 cm²) |
| | west | 2 (100 cm²) |
| | north | 4 (200 cm²) |
| summer | east | 1 (50 cm²) |
| | south | 1 (50 cm²) |
| | west | 2 (100 cm²) |
| | north | 2 (100 cm²) |
| autumn | east | 1 (50 cm²) |
| | south | 2 (100 cm²) |
| | west | 1 (50 cm²) |
| | north | 1 (50 cm²) |
| winter | east | 1 (50 cm²) |
| | south | 1 (50 cm²) |
| | west | 2 (100 cm²) |
| | north | 2 (100 cm²) |

The minimum areas at which the mortar and tile lifting defects having different depths in respective seasons in respective directions can be found from Tables 1 and 2. Accordingly, the mortar and tile defective regions can be detected at a high accuracy by dividing the area to be measured based upon the Tables representing the results.

In the present invention, in a day when it is clear at least in the daytime, a thermal image is accepted in the period of time, 19:00 in a day when it is clear at least in the daytime to 4:30 in the next day. It is determined that there is a defect at a region of the surface if the region has a temperature difference of 0.3° C. or more in comparison with the surrounding regions and has a lower temperature. Limitation of the period of time when the thermal image is accepted and of the temperature difference is determined by Experiment 2.

EXPERIMENT 2

(Basic experiment)

An experiment which will be described was conducted by using the system used in experiment 1 as shown in FIGS. 1 and 2.

In the experiment, the temperature was successively measured every 10 minutes for about 25 hours from the sunrise when it was a clear day in spring. Simultaneously, ambient temperature and sunlight exposure rate was measured.

Figure 25:
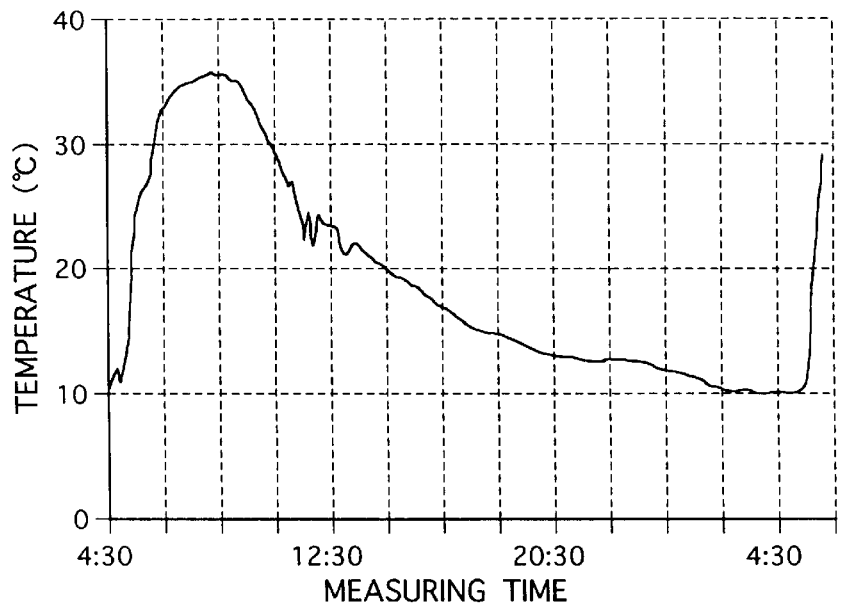
Figure 26:
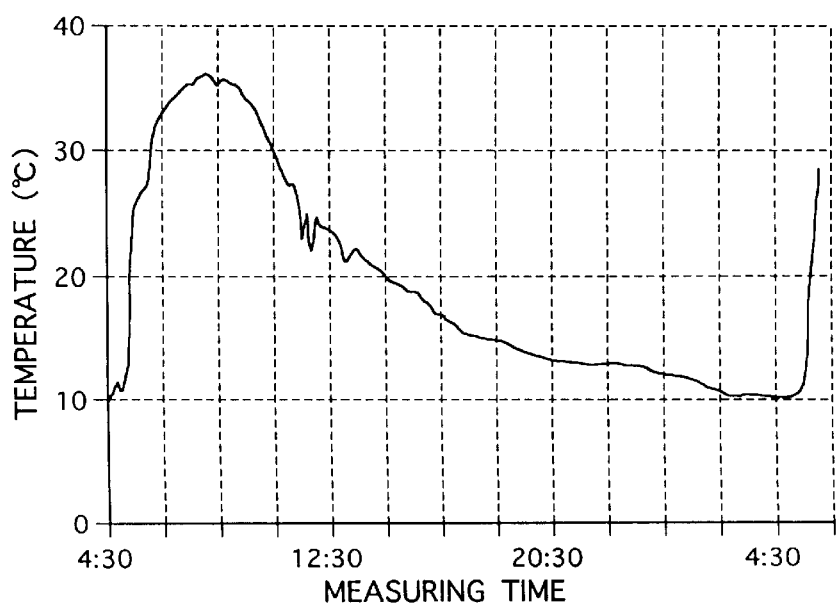

The changes in temperature of the surface of the mortar and tile separated defect having an area corresponding to 16 tiles on east side are shown in FIGS. 25 and 26, respectively. The changes in sunlight exposure rate and ambient temperature are identical with that in experiment 1 as shown in FIGS. 5 and 6, respectively. On the east side, the changes in the surface temperature of defective regions (corresponding to 32 tiles to 4 tiles) are substantially the same. However, the rate of increase or decrease in the temperature difference with the lapse of time is slightly higher as the area of the defect increases. It is found that the changes in temperature (with the lapse of time) does not have correlation with the area of the defect in the experiment and exhibits similar changes in the surface temperature. The same is applied to the other three sides although the results are not shown.

Accordingly, the results of the defect having an area corresponding to 16 tiles will be described as a representative.

On the east side, the surface temperature on the defect reaches a peak in the morning as shown in FIGS. 25 and 26 due to high sunlight exposure in the morning as shown in FIG. 5 and is remarkably lessened until the noon. The lessening of the temperature becomes low in the evening. The temperature is moderately lessened until the sunrise.

Figure 27:
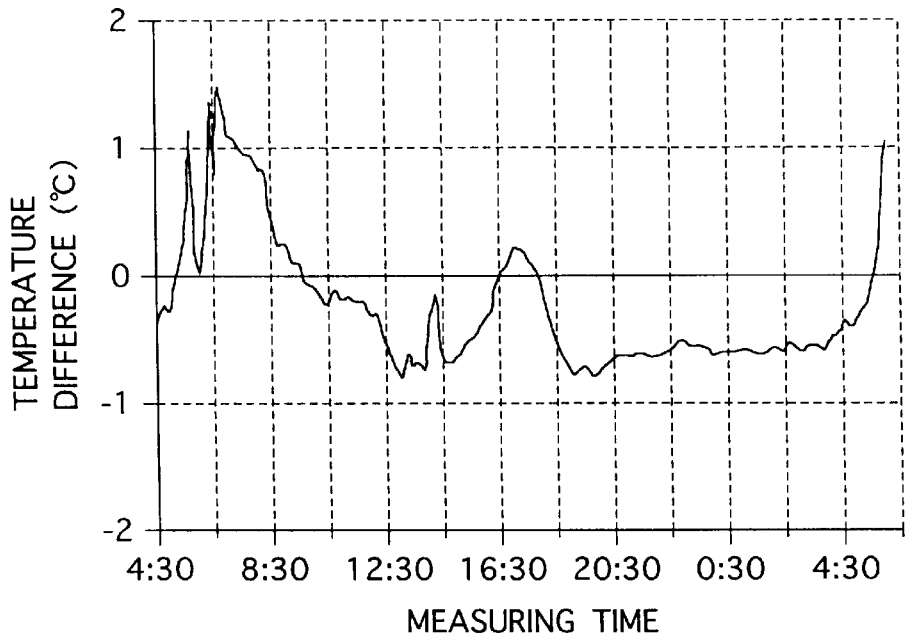
Figure 28:
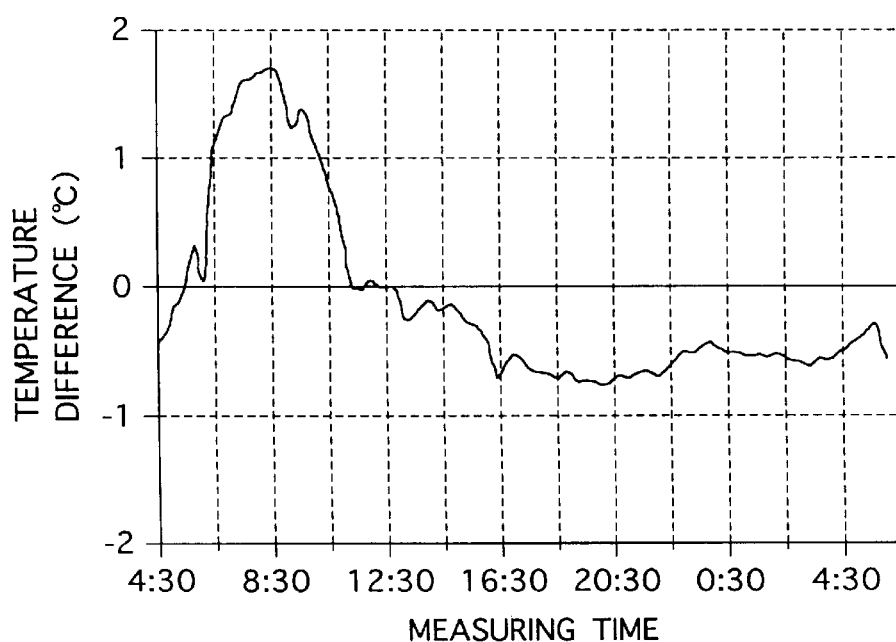

The temperature differences between the tile separated defective and non-defective region and between the mortar separated defective and non-defective regions are shown in FIGS. 27 and 28, respectively.

Referring to the changes in the temperature difference of the tile separated defect of FIG. 27, positive temperature difference in which the defect has a higher temperature difference than that of the non-defective region is exhibited before about 6 a.m. and thereafter the temperature difference peaks and then the temperature difference becomes about zero after 9:00 a.m. but before noon. The "reversal phenomenon of the temperature difference" in which the temperature difference becomes negative occurs until about 4 p.m. and then "reversal phenomenon of the temperature difference" occurs again on about 6 p.m. and it continues until about the sunrise.

Referring to the changes in the temperature difference of the mortar separated defect of FIG. 28, a positive temperature difference in which the defect has a higher temperature difference than that of the non-defective region is exhibited before about 6 a.m. and thereafter the temperature difference peaks and then the temperature difference becomes about zero after 10:00 a.m. but before noon. The "reversal phenomenon of the temperature difference" in which the temperature difference becomes negative occurs and it continues until about the sunrise.

It is found from only the results shown in FIGS. 27 and 28 that the temperature differences of the tile and mortar separated defects are high from 6 to 9 a.m. The period of time in which the temperature difference is high substantially corresponds to the period of time when the sunlight exposure is high. However, it does not correspond to the ambient temperature. On the other hand, a relatively large temperature difference is exhibited in the night although the reversal phenomenon of the temperature difference occurs. This condition continues from 19:00 in this day to 4:30 in the next day.

Figure 29:
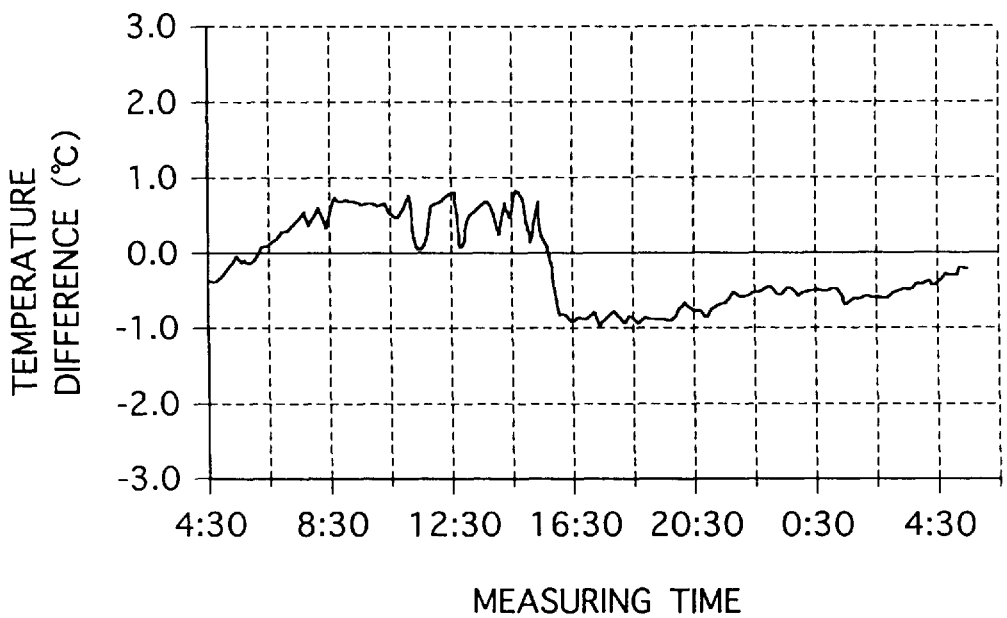
Figure 30:
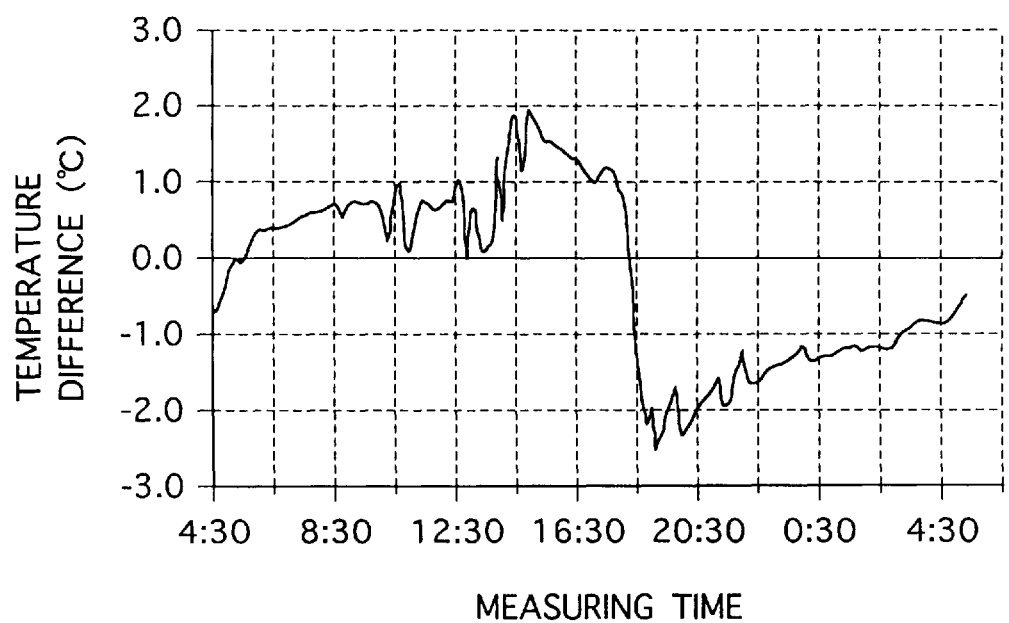
Figure 31:
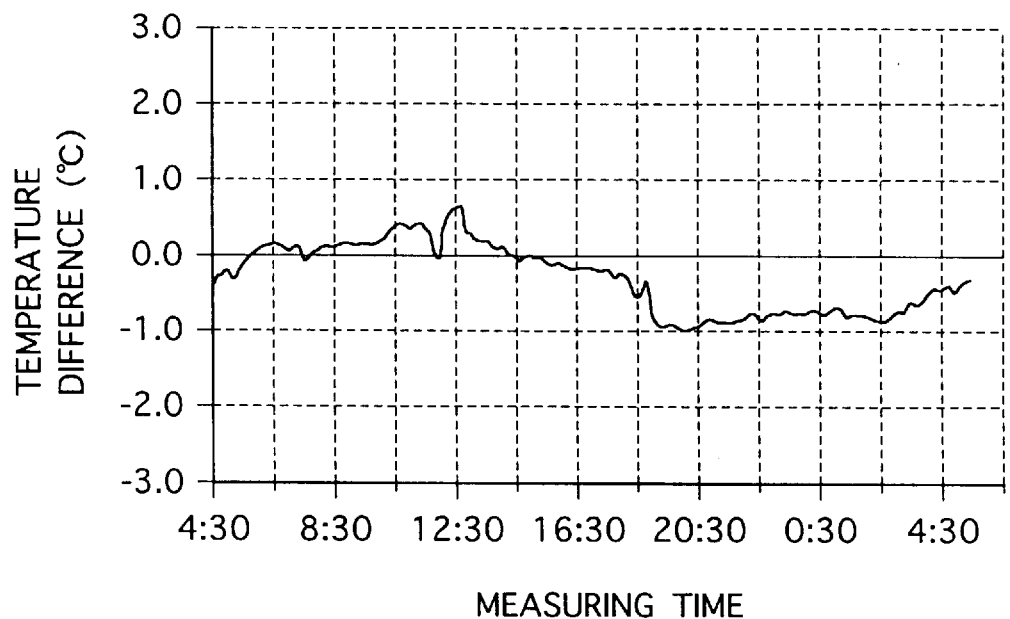

The results of FIGS. 27 and 28 show the changes in temperature difference on the east side. The results as shown in FIGS. 29 to 31 are obtained by measuring the changes in temperature differences of the mortar separated defect on the other south, west and north sides during the same experiment day.

It is found from the results that the period of time when the positive temperature difference of the east side in the daytime is largely shifted from those of south and west side. On the south side, a large temperature difference is hard to exhibit.

In contrast to this, a relatively large temperature difference is stably exhibited on any side. In particular, the negative temperature difference in the night is larger than the positive temperature difference in the day time on the north side.

Figure 32:
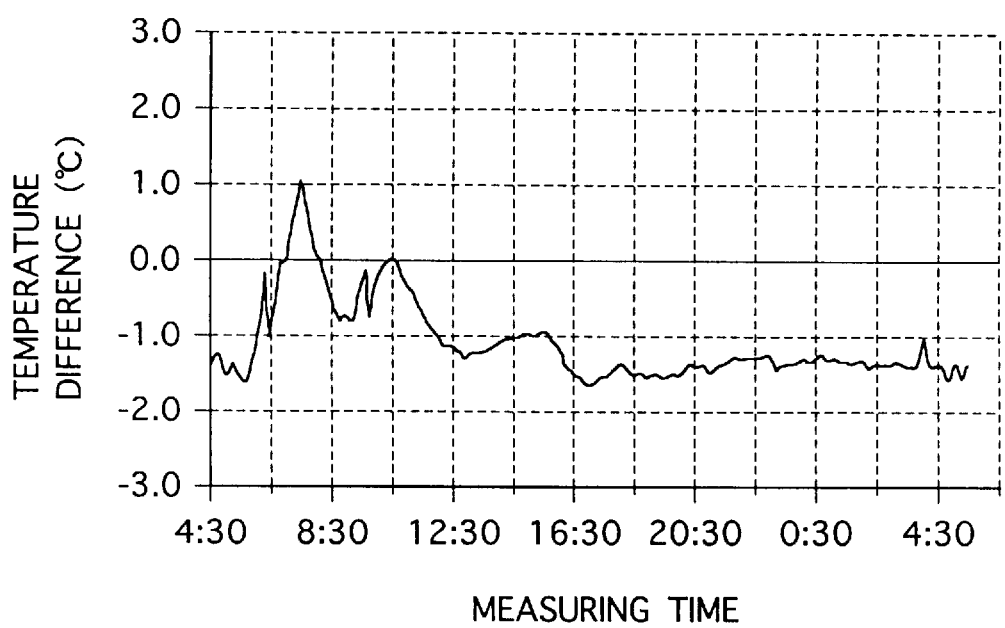
Figure 33:
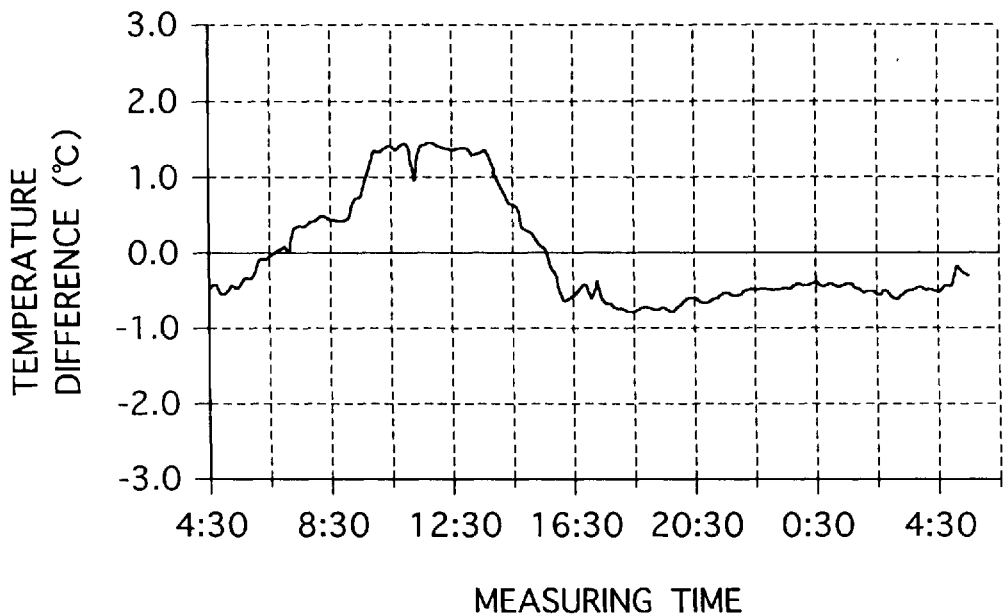
Figure 34:
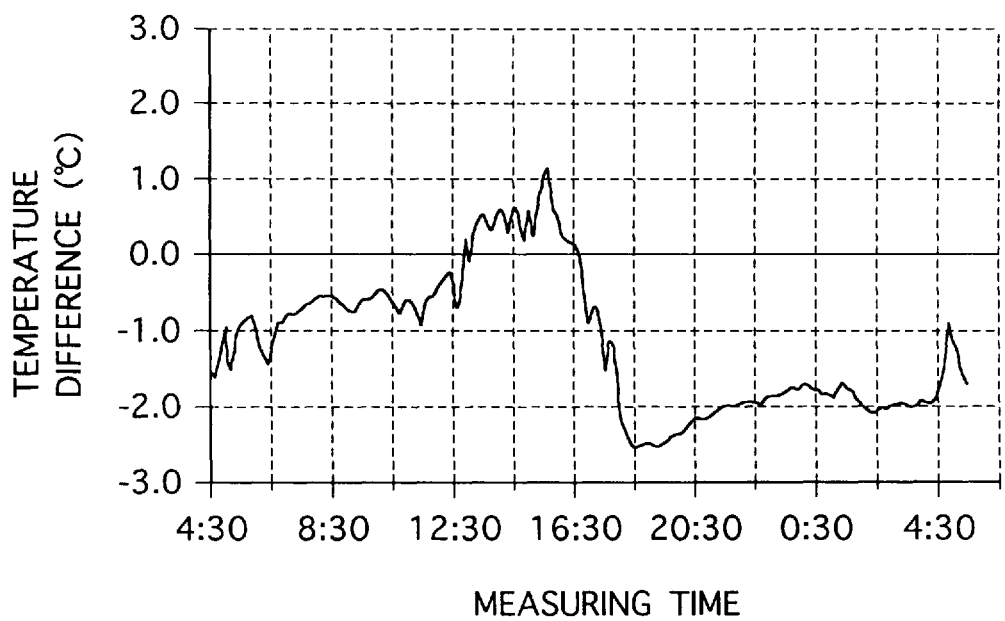

The foregoing results were obtained by the experiments in spring. Similar experiments was conducted in summer. The changes in the temperature difference of the mortar separated defect on east, south and west sides are shown in FIGS. 32 to 34. Although the results in summer are not individually described in detail, they exhibit a tendency similar to that in spring. It has been confirmed that the tendency does not change in autumn and spring.

It is found from the foregoing that a relatively large temperature difference is stably exhibited in the night, in particular in the period of time of 19:00 in the day in interest to 4:30 in the next day irrespective of the season while the changes in the temperature difference is relatively large and unstable in a peculiar period of time although a large temperature difference is exhibited in the daytime in the peculiar period of time.

(Rate of correct determination of defect)

A determination was made that there is a tile or mortar separated defect at a region having a temperature difference of 0.3° C. or more in the period of time in the daytime when the temperature difference which is peculiar to each external wall and in the period of time of 19:00 of the day in interest to 4:30 in the next day.

This determination result is compared with simulated defects in an actual model building. If the former is relevant to the latter, it is determined that the defect determination is correct. Thus, the rate of the correct defect determination is defined. The rates of the correct defect determination are shown in Tables 3 to 6. In this case, the rate of correct defect determination is shown for each area represented by the number of tiles.

The rates of correct determination of tile separated defects in the daytime, tile separated defects in the night, mortar separated defects in the daytime, and the mortar separated defects are shown in Tables 3, 4, 5 and 6, respectively.

TABLE 3

| | NUMBER OF SIMULATED SEPARATIONS | | | | |
|---|---|---|---|---|---|
| | 32 | 16 | 8 | 4 | 32~4 |
| east side | 87.5 | 100 | 100 | 100 | 93.3 |
| south side | 21.9 | 100 | 100 | 100 | 58.3 |
| west side | 0 | 0 | 0 | 0 | 0 |
| north side | 56.3 | 75.0 | 12.5 | 0 | 51.7 |
| average | 41.4 | 68.8 | 53.1 | 50.0 | 50.8 |

Sampling time:
east side 6:59, south side 8:51, west side 14:36, north side 11:29

TABLE 4

| | NUMBER OF SIMULATED SEPARATIONS | | | | |
|---|---|---|---|---|---|
| | 32 | 16 | 8 | 4 | 32~4 |
| east side | 100 | 100 | 100 | 50.0 | 96.7 |
| south side | 93.8 | 87.5 | 75.0 | 0 | 83.3 |
| west side | 50.0 | 75.0 | 100 | 50.0 | 63.3 |
| north side | 65.6 | 81.3 | 87.5 | 100 | 75.0 |
| average | 77.4 | 86.0 | 90.6 | 50.0 | 79.6 |

Sampling time:
east side 2:17, south side 2:58, west side 4:20, north side 22:17

TABLE 5

| | NUMBER OF SIMULATED SEPARATIONS | | | | |
|---|---|---|---|---|---|
| | 32 | 16 | 8 | 4 | 32~4 |
| east side | 87.5 | 100 | 100 | 100 | 93.3 |
| south side | 87.5 | 75.0 | 100 | 100 | 80.0 |
| west side | 100 | 100 | 100 | 100 | 100 |
| north side | 50.0 | 100 | 0 | 0 | 53.3 |
| average | 81.3 | 93.8 | 75.0 | 75.0 | 81.7 |

Sampling time:
east side 6:59, south side 8:51, west side 14:36, north side 11:29

TABLE 6

| | NUMBER OF SIMULATED SEPARATIONS | | | | |
|---|---|---|---|---|---|
| | 32 | 16 | 8 | 4 | 32~4 |
| east side | 100 | 100 | 100 | 100 | 100 |
| south side | 100 | 100 | 100 | 100 | 100 |
| west side | 100 | 100 | 100 | 100 | 100 |
| north side | 100 | 100 | 100 | 100 | 100 |
| average | 100 | 100 | 100 | 100 | 100 |

Sampling time:
east side 2:17, south side 2:58, west side 4:20, north side 22:17

It is found from Table 3 to 6 that the rate of correct determination of the tile separation defect of 4 or more tiles which are necessary to repair is as low as 50.8% as an average. On the other hand, the rate of the correct determination in the night time is as high as 79.6%. The rate of the correct determination of mortar separation defect is 81.7% in the daytime while it is 100% in the night.

It is found from a summary of the results that detection of the mortar separation defect is easier than that of the tile separation defect and that the determination of the defect in the night is more correct than that in the daytime.

Experiments which are similar to the above-mentioned experiment were also conducted in summer and autumn. It was clear in the summer experiment day while it was cloudy in the autumn experiment day.

The rates of the correct determination of the tile separation defect in the summer experiment in the daytime and night are 80.0% and 81.3%, respectively. The rates of the correct determination of the mortar separation defect in the daytime and night are 91.7% and 96.7%, respectively. It is found from these results that the detection of the mortar separated defect is easier than that of the tile separation defect.

On the other hand, the rates of the correct determination of the tile separation defect in the summer experiment in the daytime and night are 73.3% and 48.8%, respectively. The rates of the correct determination of the mortar separation defect in the daytime and night are 90.8% and 75.8%, respectively. The reason why the rate of the correct defect determination is low in the night is due to the fact that since there was no sunlight exposure in the daytime, the amount of the reserved heat is so reduced that a temperature difference occurs. Accordingly, the detection of the defect when it is cloudy or rainy all day should be avoided.

Now, a basic method of detecting a defect of the present invention using the differential temperature distribution will be described. An infrared radiometric thermometer (thermal image sensor) is provided in such a manner that it faces the surface of a structure to be measured. The thermal energy radiated from the surface of the structure to be measured is detected by the infrared radiometric thermometer. A signal from the thermometer is fed to an image analyzing device. The temperature in an image range and the temperature distribution image is obtained. A portion having a temperature which is different from that of another area is extracted so that the portion is determined as a defective portion.

In the present invention, measuring of the thermal energy is conducted by means of the infrared radiometric thermometer during daytime and night so that thermal images during both times are obtained. Then, in the image analyzing device, a substraction-processed image is obtained by subtracting the temperature distribution image which is obtained during the night from the temperature distribution image which is obtained during the daytime. A portion having a higher temperature than that of another portion is extracted and determined as a defective portion by the subtraction processing. Since the temperature distribution between the defective portion and the non-defective portion is enhanced by the subtraction processing, detection of the defective portion is easy.

Furthermore, an integration processed image is obtained by integrating the subtraction-processed image. A portion having a higher temperature than that of the other portion in the integration-processed image is extracted and determined as a defective portion. The temperature difference between the defective portion and the non-defective portion is further enhanced so that detection of the defective portion becomes easier.

Processing such as the above-mentioned subtraction-processing and the time-integration processing can be easily conducted by using a thermal image processing software "TVS-2000" commercially available from Nippon Avionics Co., Ltd. It can be determined that there is a defect in a area having a lower temperature which is different by not less than ±0.3° C. than the other area. Using the subtracted image and subtracting image, it is determined that there is a defect at an area having a higher temperature. It is found from the other many experiments that the possibility of wrong determination of the defect which is made with reference to not higher than ±0.3° C. temperature becomes higher.

EXPERIMENT 3

(Basic Experiment)

Figure 35:
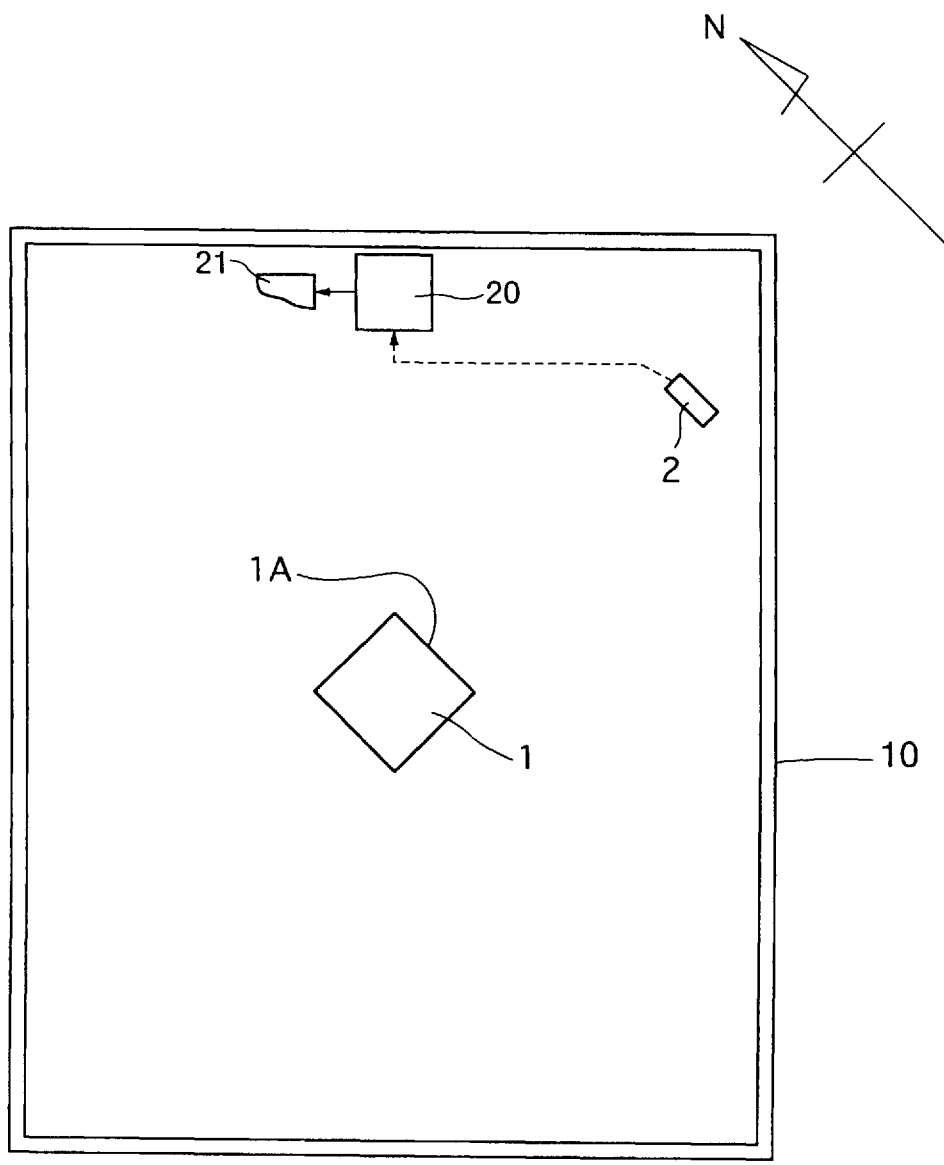
FIG. 35 is a schematic view showing a system in which the present invention is embodied.
Figure 36:
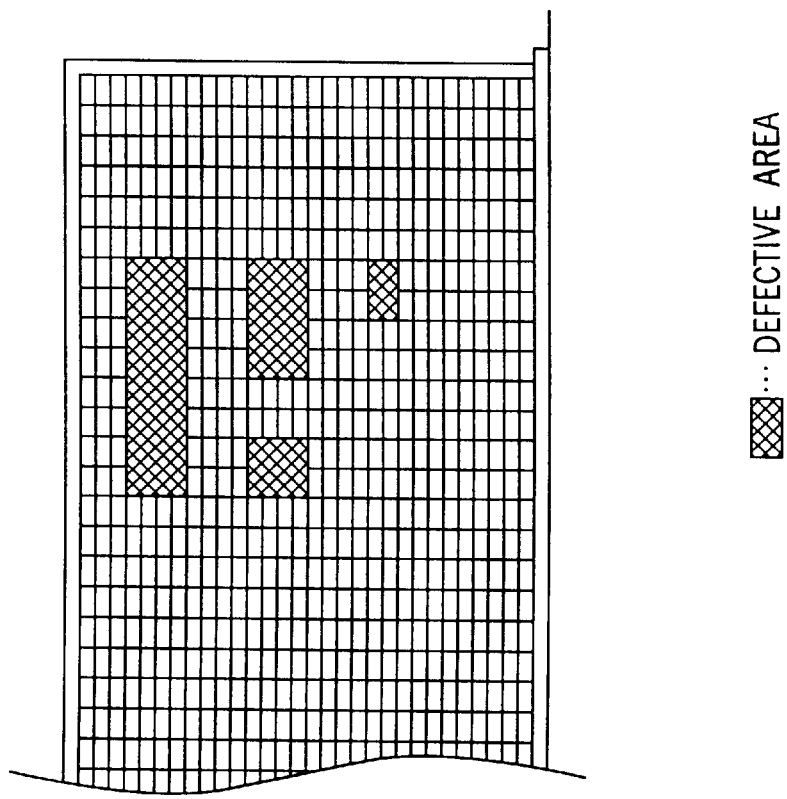
FIG. 36 is a schematic view showing an example of a wall of a structure to be measured.

A model structure 1 with sides, each having a width of 5 m and a height of 1.8 m on which new small tiles are applied is built on the roof on building existing at a rural city as shown in FIG. 35. As shown in FIG. 36, a simulated defective portion (tile separated portion) having a 7% area is artificially formed on an external wall 1A of the model structure 1. The simulated defective portion comprised an area of 32 tiles, an area of 16 tiles, an area of 8 tiles and an area of 4 tiles in order to enable a determination of whether there is a temperature difference due to a difference in area of the defective area. The area of 7% is an average value which is found by actual tile defect investigation.

In order to detect the defect of the external wall, an infrared radiometric thermometer (thermal image sensor) 2 which faces the external wall 1A is placed on the roof.

A signal from the thermometer 2 is input to an image analyzing device 20. The analyzed result is displayed on a CRT display 21 or is recorded on a floppy disk and the like.

In the thus formed system, the infrared radiation energy from the external wall 1A is detected by the infrared radiation thermometer 2. An average temperature of each of unit is obtained by dividing the measured area and presence or absence of a defect is determined based upon the temperature difference between adjacent unit areas.

In the experiment, measurements were conducted by means of an infrared radiometric thermometer successively every 10 minutes for about 25 hours beginning with the sunrise on a clear day in spring.

Figure 37:
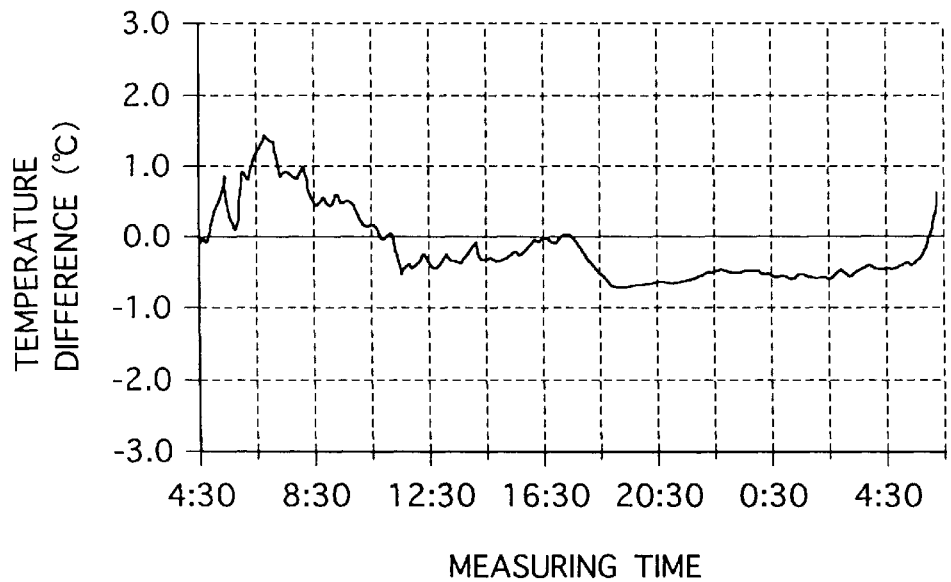
FIGS. 37 and 38 are graphs showing the results of the experiments of the present invention.
Figure 38:
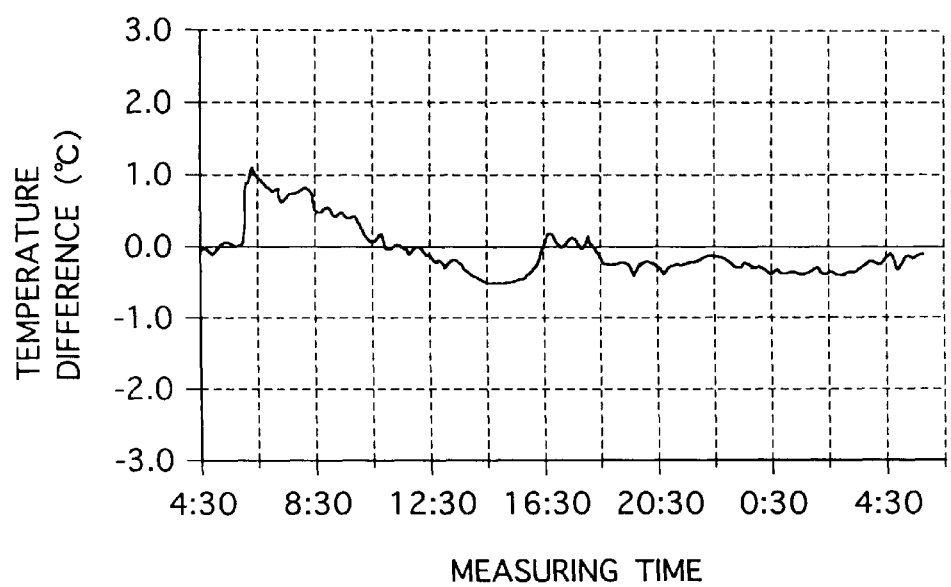

The changes in surface temperature of the defect having an area corresponding to 32 tiles are shown in FIG. 37. The changes in surface temperature of the defect having an area corresponding to 8 tiles are shown in FIG. 38.

As is apparent from FIG. 37, the defect having an area corresponding to 32 tiles exhibits a temperature which is different by not higher than 0.3° C. from that of a surrounding area in a short period of time between 4:30 to 6:00, 10:00 to 11:30, 15:00 to 17:30. Detection of the defect can be conducted during other times, specifically almost all times, such as for 20 hours a day.

However, the defect having an area corresponding to 8 tiles exhibits a temperature which is different by not less than 0.3° C. from that of the surrounding area in every shortened period of time, for example, 8:30 to 9:30, 13:00 to 15:30, 0:00 to 3:00. Detection of the defect can be conducted for 9.5 hours a day, the period of time of which is shorter than that when the detection of the defect can be made, unlike the detection of the defect in a 32 tile area.

Figure 39:
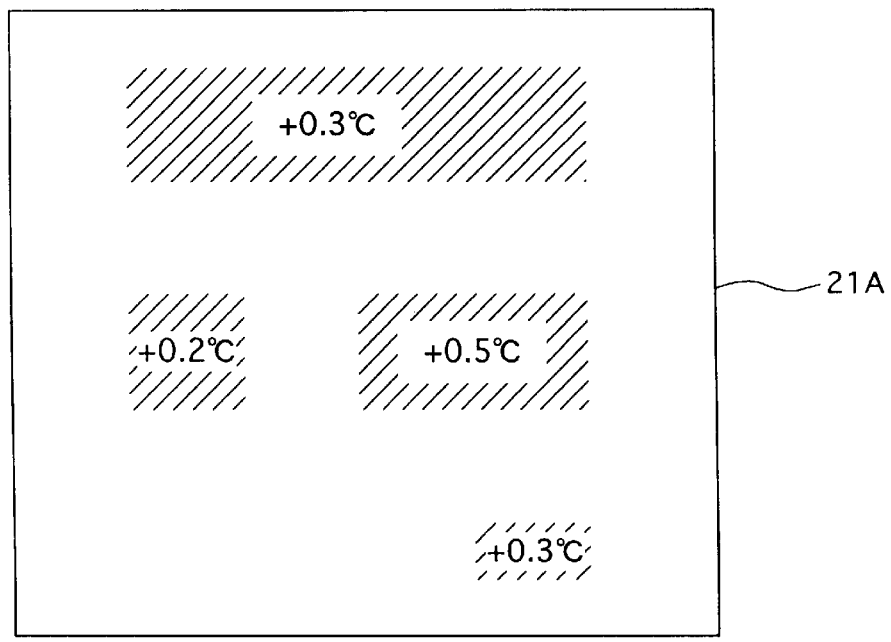
FIGS. 39 to 41 are schematic views showing thermal images of the wall of structures to be measured.
Figure 40:
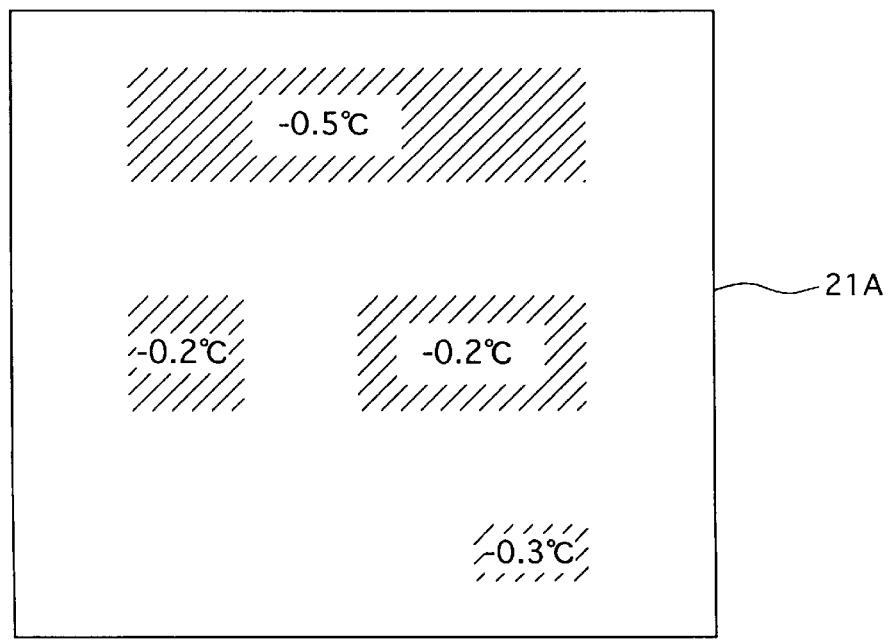
Figure 41:
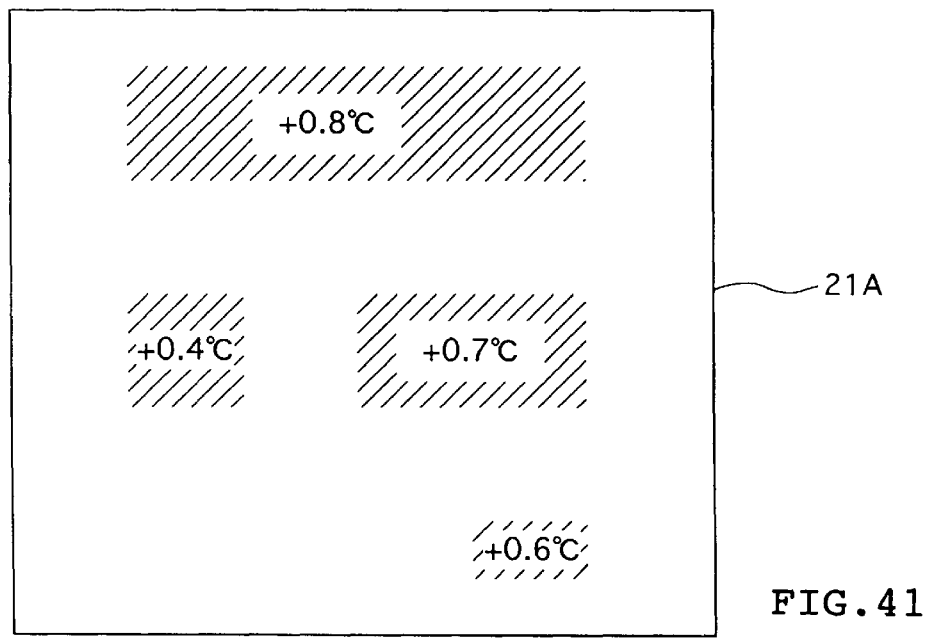

Therefore, a subtraction operation is conducted between the temperature distributions of the structure surface, which are detected during the daytime and night in accordance with the present invention. The process of the subtraction operation will be described with a reference to thermal images displayed on the CRT display 21A which are schematically shown in FIGS. 39 to 41. The thermal images representative of the temperature distributions of the surface of the model structure 1 which were detected at 10:00 in the daytime and 23:00 in night are shown in FIGS. 39 and 40, respectively.

The area corresponding to 8 tiles can not be determined to be defective from the temperature distributions shown in FIGS. 39 and 40 by consideration of an error since it is different in temperature by +0.2° C. and −0.2° C., respectively from that of the surrounding area. If the subtraction operation is conducted by subtracting the thermal image shown in FIG. 40 from the thermal image shown in FIG. 39 by means of an image analyzing device, the temperature difference of the area corresponding to 8 tiles is enhanced to +0.4° C. as schematically shown in FIG. 41, so that the defect can be detected at a higher accuracy.

The temperature difference of the area corresponding to 4 tiles is enhanced to +0.6° C. by integrating the image shown in FIG. 39 for the image shown in FIG. 41. The detection accuracy can be further enhanced.

On the other hand, the temperature difference of the area corresponding to 32 tiles is enhanced to +0.8° C. The detection accuracy can be enhanced.

(Applied Experiment)

In order to confirm whether the result of the above-mentioned experiment 3 is applicable to an actual bridge, an applied experiment was conducted in a bridge which is in practical use. This applied experiment was conducted for a bridge in a highway across a first class river in the Tokyo area.

Figure 42:
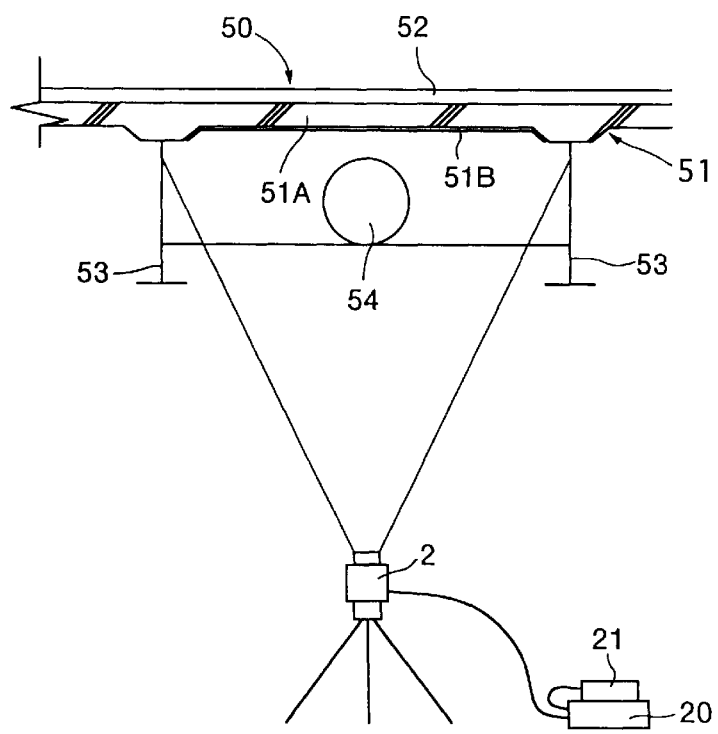
FIG. 42 is a schematic view showing a bridge used for the experiments of the present invention.
Figure 43:
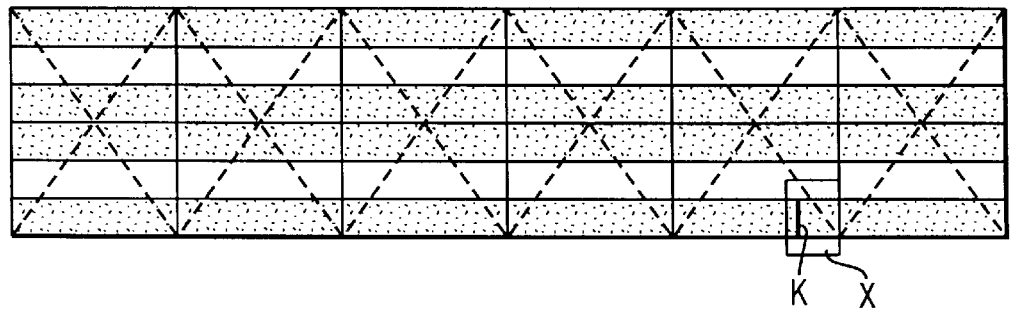
FIG. 43 is a bottom view showing a steel plate reinforced floor slab for the bridge.

As shown in FIG. 42, the bridge 50 comprises a floor slab 51 having a concrete floor slab 51A to which reinforcing steel plates 51B are bonded on the lower side thereof. A pavement road 52 is formed on the floor slab 51. The floor slab 51 is supported on a main girder 53. Water supply main tubes 54 extend under the floor slab 51. The bottom of the bridge is schematically shown in FIG. 43 to have a given longitudinal area having two lanes. In the area shown in FIG. 43, the tapping method was preliminarily conducted in which the reinforcing steel plates are tapped with a test hammer while using a boom vehicle. Detective area K was marked with a chalk. It was presumed that this defective portion K is a portion in which bonding agent is separated over about 500 cm².

In the experiment shown in FIG. 42, an infrared radiometric thermometer 2 is placed on the ground below the bridge. The thermal radiation energy from a portion of bridge 50 is computed by the thermometer 2. Similarly to the model experiment, the signal from the infrared radiometric thermometer 2 is analyzed by an image analyzing device 20 and is displayed on a CRT display 21 if necessary.

Then, the temperature difference between the detective portion and non-detective portion is determined by the image analyzing device 20. The measuring is conducted about every 10 minutes for 24 hours. The result is shown in FIG. 44.

Figure 44:
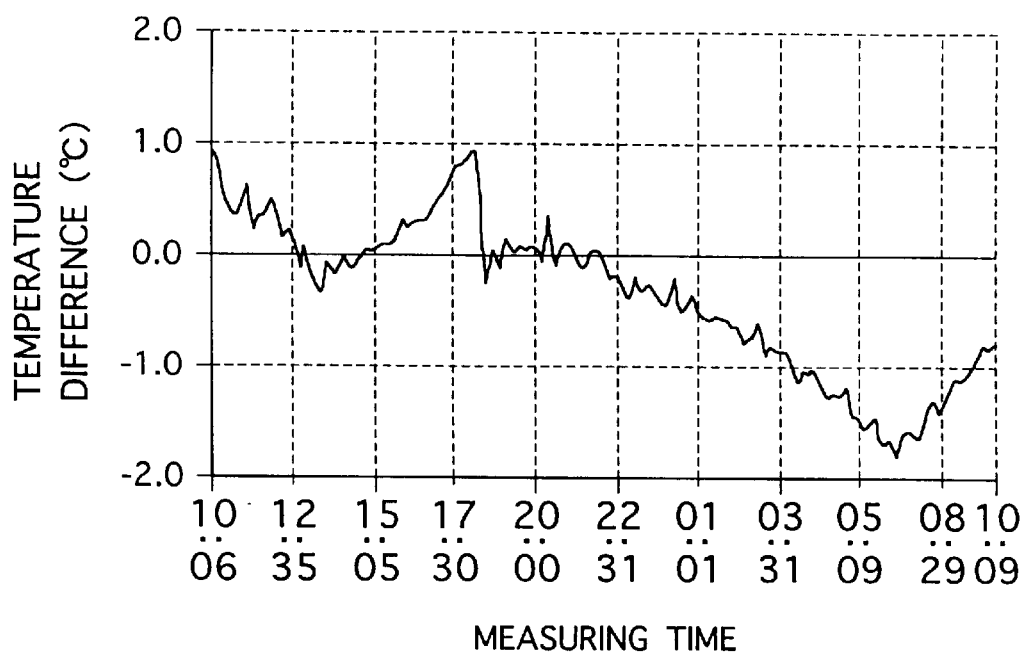
FIG. 44 is a graph showing the result of the experiment of the present invention.

It is found from FIG. 44 that the temperature difference between the defective and non-defective areas is not less than 0.3° C. during 1:00 to 10:00. It is relatively easy to detect the defect for the period of time, since it is possible to clearly make difference between the defective and non-defective areas. If the measurement is conducted at 22:00 when the temperature difference is ±0.0 C., it is impossible to detect the defect.

Accordingly, a subtraction operation between the thermal images which were detected at 12:00 in day time and at 23:00 in night is conducted. The temperature difference between the defective area and the surrounding area is about 1.0° C. so that the defective area can be detected at a higher accuracy. If the thermal image which was differential-operated was integrated for time, the temperature difference between the defective area and the surrounding area is 1.5 C. Defect detection can be conducted at a higher accuracy.

The result of the above-mentioned applied experiment shows that the method of detecting the defect of the structure which was conducted in the basic experiment can be used for the detection of the defect of the steel plate reinforced structure and is applicable to the actual bridge.

The basic method of detecting defect a structure which is reinforced with steel plates of the present invention is conducted as follows; An infrared radiometer thermometer (thermal image sensor) is provided to face the surface of the structure to be measured. The infrared radiation energy from the surface is detected. The detected signal is fed to an image analyzing device in which a contour map representing temperature difference is prepared based upon the measured temperatures at respective areas.

In this case, as a reference temperature which is a reference for a temperature difference, an average temperature in a given imaged area at a measuring time is adopted. Or a minimum temperature (excluding a temperature which is remarkably different from the average temperature) in a group of unit areas which are segmented from an imaged area at a measuring time may be adopted. Or the temperature at an area where the temperature does not change over a given length in a graph showing the temperature difference may be adopted, since the area of the defect portion is smaller than that of the non-defective area. These adopted reference temperature are not substantially different.

On the other hand, it is necessary to obtain the correlation between the area in the contour map and the actually measured surface (reinforcing steel plate surface) since they are relevant in the contour map of the temperature difference. Hence, in practice, it is possible to determine whether or not the area having a temperature difference of 0.3° C. or more is not less than 400 $cm^2$ of the measured area by measuring the distance between the position of the infrared radiometric thermometer and the measured steel plate surface by means of measuring instrument or by making the area of the current image proportional to the area of the steel plate by also considering the angle of the depression or elevation if the position of the infrared radiometric thermometer has been known on the map. In this case, the magnification of the lens used should also be considered.

Thus, if the area of the detected surface is more than 400 $cm^2$, it is determined that there is a defect in this area. The limitation of the area of the measured surface and the temperature difference is determined by the following model experiment which is described in detail.

EXPERIMENT 4

(model experiment)

Figure 45:
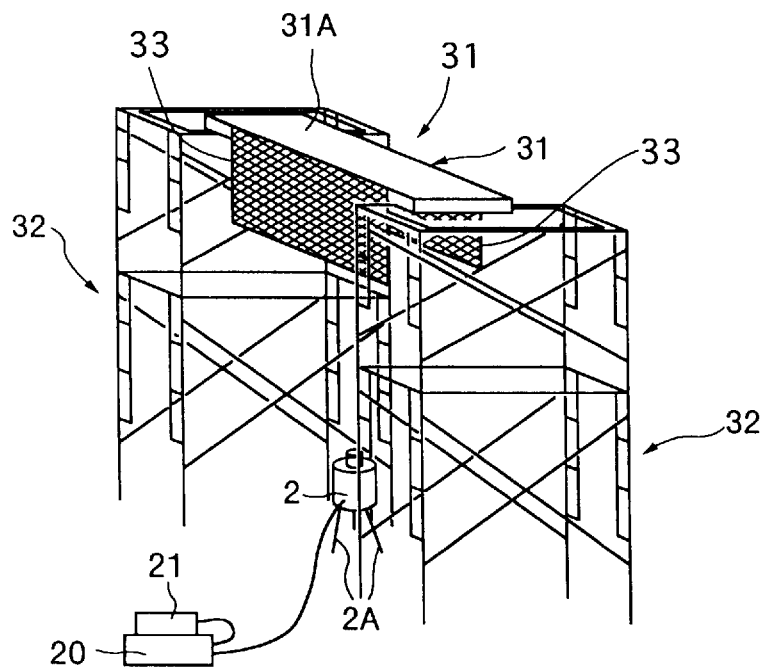
FIG. 45 is a schematic view showing a model structure used for the experiment of the present invention.

A model of a bridge is made as a steel plate reinforced structure as shown in FIG. 45. A steel plate reinforced floor slab 31 comprising a floor slab 31A made of precast concrete having a width of 1 m, a length of 2.5 m and a thickness of 15 cm, to which a reinforcing steel plate 31B having a width of 40 cm, a length of 2 m and a thickness of 6 mm is bonded with epoxy resin is disposed on scaffolds 32. Concrete panels 33 are suspended from the opposite sides of the floor slab 31, for simulating a main girder of an actual bridge.

The steel plate reinforced floor slab 31 is disposed so that the reinforcing plate 31B is located on the lower side of slab 31. An infrared radiometric thermometer 2 is mounted on a tripod 2a so that it is below the reinforcing steel plate 31B and its sight line is aligned with the steel plate reinforcing floor slab 31. The thickness of steel plate 31B is a standard thickness of the plate which is practically used in bridges.

Figure 46:
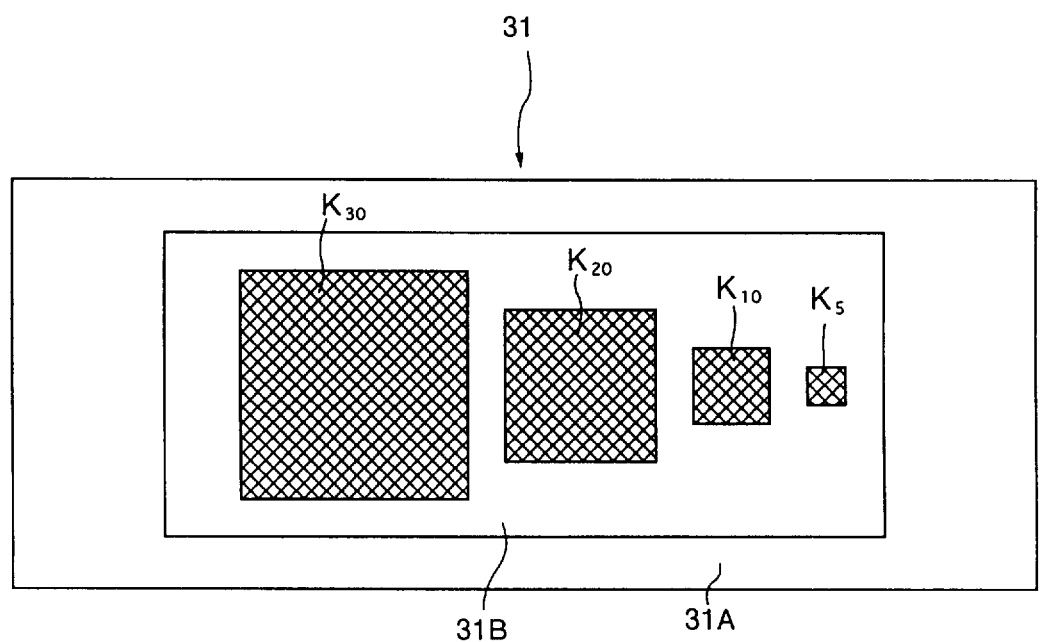
FIG. 46 is a bottom view showing a steel plate reinforced floor slab which is formed with a simulated defected region.

The steel plate reinforced floor slab 31 is intentionally formed with a portion which is not filled with epoxy resin as a defect. The simulated defect comprises four simulated defects K30, K20, K10, K5, which are 30 cm square, 20 cm square, 10 cm square and 5 cm square, respectively as shown in FIG. 46.

A signal from the infrared radiometric thermometer 2 is analyzed by an image analyzing device 20 and is displayed on a CRT display 21 if necessary.

In the thus formed system, the difference in temperature between the simulated defects and non-defective area (which is filled with an epoxy resin) is determined by detecting the infrared radiation energy from the reinforcing steel plate 31B. The measurement is carried out above every 10 minutes for 23 hours. The results of the temperature differences of the 10 cm square simulated defects K10 and non-defective area are shown in FIG. 47 and the results of the temperature differences of 20 cm square simulated defective area K20 and non-defective area are shown in FIG. 48.

Figure 47:
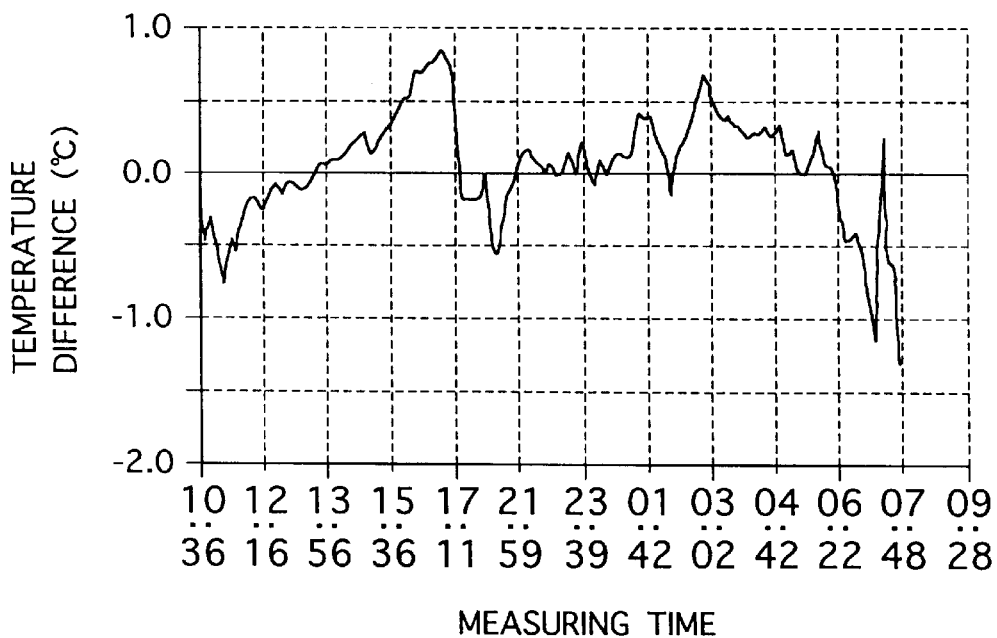
FIGS. 47 to 49 are graphs showing the result of the experiment of the present invention.

Referring now to FIG. 47, the temperature difference is relatively stably no less than about 0.3° C. in a period of 1 hour of 6 to 7 a.m., 1 hour of 11 to 12 a.m., 1 hour of 14 to 15 p.m. and 1.5 hour of 15.30 to 17 p.m., if the area of the defect is 100 $cm^2$, temperature difference is less in the other hours. The period of time in which the temperature difference is not less than 0.3° C. is short.

Figure 48:
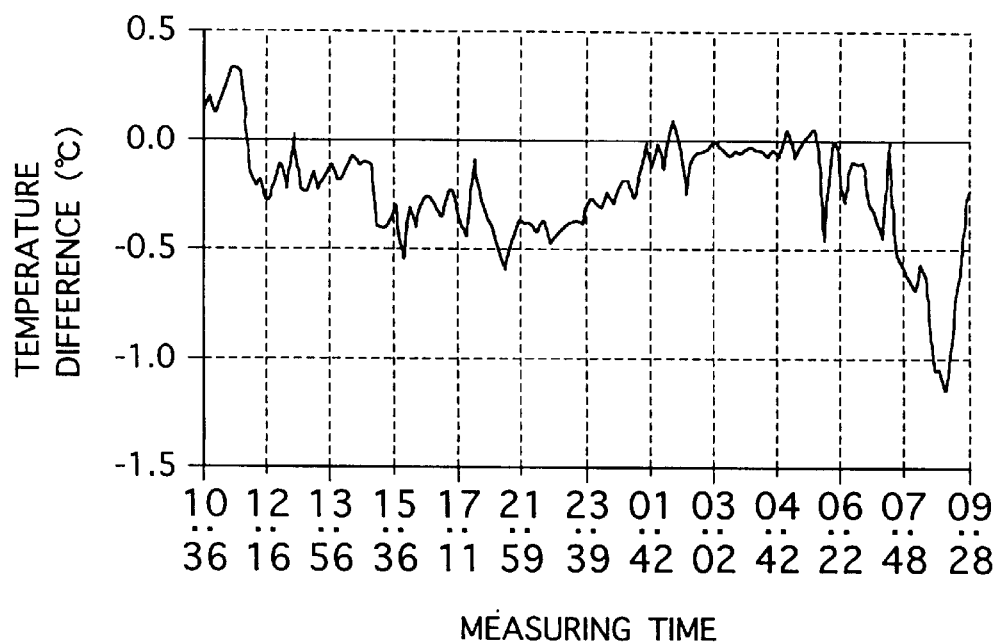

In contrast to this, the result shown in FIG. 48 in which the area of the defective portion in 400 $cm^2$ shows that the temperature difference is not less than −0.3° C. for 8 hours between 15 to 23 p.m. and for 2 hours between 7 to 9 a.m.

It is found from these results that the temperature difference is unstably not less than 0.3° C. or not higher than 0.3° C. depending upon the measuring hours if the area of the defective portion is 100 $cm^2$. This tendency is more remarkable if the area of the defective portion is 25 $cm^2$. Therefore, considering the practical detection whether or not any defect is present upon basis of the temperature difference, this method is not suitable for detection of a defect having a small area.

In contrast to this, the presence or absence of a defect can be stably determined with reference to the temperature difference of 0.3° C. provided that the measurement is conducted in these long periods of time when the temperature difference is not less than 0.3° C. if the area of the defect is 400 $cm^2$. It is found that the same is applied to the case in which the area of the defect is 900 $cm^2$.

Referring to FIG. 48 again, the temperature of the non-defective area is lower than that of the separated area and the temperature difference is large for 8 hours between 15 and 23 p.m. It is deemed that this is due to the fact that the sunlight exposure and the change in the temperature of the external atmosphere is relatively low and the disturbance is less. In contrast to this, FIG. 47 shows the tendency that the temperature difference is less for one day and the change in temperature difference is random. This tendency is due to the fact that sunlight exposure and the change in the temperature of the external atmosphere is influenced so that the temperature difference and the change in the temperature difference is vague since the area of the defective portion is less.

Therefore, in accordance with the present invention, the presence of a defect is determined with reference to the temperature difference not less than 0.3° C., which is measured during preferably 15 to 23 p.m., more preferably 18 to 23 p.m. when the amount of sunlight is less. It is preferable to totally determine the presence or absence of a defect by measuring the temperature difference at different times. It is found from the many various experiments that the possibility of wrong determination of defect is higher when the determination of the presence of the defect is made with reference to the temperature difference not higher than 0.3 C.

(Applied Experiment)

In order to confirm whether the result of the above-mentioned basic experiment is applicable to the steel plate reinforced structure, an applied experiment was conducted in an actually used bridge, which is a steel plate reinforced structure. The experiment was conducted for the bridge similarly to Experiment 3. The defect K was presumed as shown in FIG. 43.

In the experiment, an infrared radiometric thermometer 2 is placed on the ground so that it is located below the bridge as shown in FIG. 42. The thermal radiation energy from a given area is measured by the thermometer 2. A signal from the thermometer 2 was analyzed in the image analyzing device 20 and was displayed on a CRT display 21.

A temperature difference between the defective area which was detected by the tapping method and non-defective area was determined. The measurement was conducted about every 10 minutes for about 24 hours. The result is shown in FIG. 49.

Figure 49:
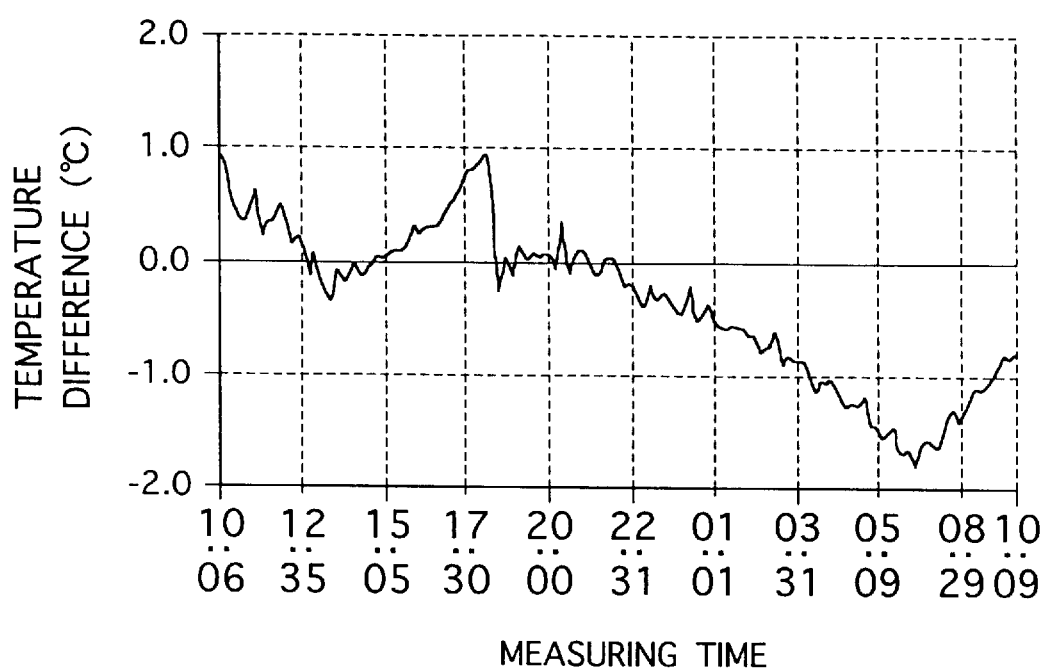

It is found from FIG. 49 that the temperature difference between defective portion and non-defective portion is not less than $-0.3°$ C. from 1 a.m. to 10 a.m. Accordingly, it is found from this experiment that the defect in a steel plate reinforced structure can be properly detected with reference to the temperature difference.

The present invention can be applied to the diagnosis of roof, fume stack, dam site, bank, road (high level road) as well as the above-mentioned diagnosis of the external wall of building. Defects such as cracks, separation and lifting can be detected.

In case in which the structure to be measured is steel plate reinforced structure, the method of the present invention can be used on a building, roof, fume stack, dam site, bank, tunnel, subway, road (high level road) which is reinforced with steel plate in addition to the above-mentioned diagnosis of the bridge.

What is claimed is:

1. A method for detecting a defect of an outdoor structure by measuring the radiation energy from the structure using an infrared radiometric thermometer, said method comprising the steps of:
    measuring the temperature of a surface of said structure using said infrared radiometric thermometer in a period of time from 19:00 on one day to 4:30 on the next day when it is clear at least in the daylight existing in said period of time; and
    determining that there is a defect at a region of the surface if the region is different in temperature by at least $0.3°$ C. than the temperature of a surrounding region and has a lower temperature than the temperature of the surrounding region.

2. A method for detecting a defect as defined in claim 1 including the step of measuring the area of the region of the surface having a temperature difference of at least $0.3°$ C., and wherein the determining step is further defined in that if the region having a temperature difference of at least $0.3°$ C. with respect to surrounding regions is 200 $cm^2$ or higher in area, a determination is made that there is a defect at the region and if it is less than 200 $cm^2$, a determination is made that there is no defect or the defect is neglected.

3. A method for detecting a defect of a structure as defined in claim 2 in which, when said structure is reinforced with steel plates which are integral with a concrete slab on the surface thereof, the determining step is further defined as one in which a determination is made that there is a defect at a region of the steel plates having a temperature difference of at least $0.3°$ C., in comparison with that of a surrounding region if the area of the region of the steel plates is 400 $cm^2$ or higher and a determination is made that there is no defect or the defect is neglected if the area of the region of the steel plates is less than 400 $cm^2$.

4. A method for detecting a defect as defined in claim 1 in which the measuring of the temperature of the surface of the structure is carried out at least once in the daylight in said 19:00 - 4:30 period of time and at least once again in said 19:00 - 4:30 period of time and in which determination of the defect is made based upon the results of both measurements.

5. A method for detecting a defect as defined in claim 1 wherein the measuring step is further defined as measuring the temperature of the surface of the structure in the daylight and night and the determining step is further defined as determining that there is a defect at a region of the surface if the temperature difference between the region and a surrounding region for the temperatures which are measured in the daylight and night is at least $-0.3°$ C. for temperatures measured in the night and is at least $+0.3°$ C. for temperatures measured in the daylight.

6. A method for detecting a defect as defined in claim 1:
    wherein the measuring step is further defined as measuring the temperature of the surface of the structure in the daylight and night of said period of time to obtain the temperature distributions over the surface at the respective times;
    wherein the method includes the step of performing a differential operation between these temperature distributions to obtain a differential temperature distribution; and
    wherein the determining step is further defined as determining a defect of the structure based upon the differential temperature distribution.

7. A method for detecting for defect of a structure as defined in claim 6 in which an integrated temperature distribution is obtained by integrating said differential temperature distribution over time and in which the determining of the defect of the structure is based upon the integrated temperature distribution.

8. A method for detecting a defect of a structure as defined in claim 7 wherein the measuring step is further defined as one in which measurement of the temperature is performed at a plurality of different times; and the determining step is further defined as determining that there is a defect at a region of the surface if the region has an integrated temperature difference of at least $\pm 0.3°$ C.

9. A method for detecting a defect of a structure as defined in claim 6 wherein the measuring step is further defined as one in which measurement of the temperature is performed at a plurality of different times; and the determining step is further defined as determining that there is a detect at a region of the surface if the region has a differential temperature of at least $\pm 0.3°$ C.

* * * * *